US009856449B2

(12) United States Patent
Lovley et al.

(10) Patent No.: US 9,856,449 B2
(45) Date of Patent: Jan. 2, 2018

(54) MICROBIAL PRODUCTION OF MULTI-CARBON CHEMICALS AND FUELS FROM WATER AND CARBON DIOXIDE USING ELECTRIC CURRENT

(71) Applicant: UNIVERSITY OF MASSACHUSETTS, Boston, MA (US)

(72) Inventors: Derek R. Lovley, Amherst, MA (US); Kelly P. Nevin, Amherst, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 319 days.

(21) Appl. No.: 14/860,211

(22) Filed: Sep. 21, 2015

(65) Prior Publication Data

US 2016/0130549 A1  May 12, 2016

Related U.S. Application Data

(62) Division of application No. 13/514,378, filed as application No. PCT/US2010/061690 on Dec. 22, 2010, now Pat. No. 9,175,408.

(60) Provisional application No. 61/289,349, filed on Dec. 22, 2009.

(51) Int. Cl.
| | |
|---|---|
| C12M 1/42 | (2006.01) |
| C12M 1/34 | (2006.01) |
| C12M 1/00 | (2006.01) |
| C25B 3/00 | (2006.01) |
| C12P 7/40 | (2006.01) |
| C12P 7/54 | (2006.01) |
| C12P 7/16 | (2006.01) |
| C25B 3/04 | (2006.01) |
| H01M 8/16 | (2006.01) |

(52) U.S. Cl.
CPC ............ *C12M 35/02* (2013.01); *C12M 21/12* (2013.01); *C12M 41/00* (2013.01); *C12P 7/16* (2013.01); *C12P 7/40* (2013.01); *C12P 7/54* (2013.01); *C25B 3/00* (2013.01); *C25B 3/04* (2013.01); *H01M 8/16* (2013.01); *Y02E 50/10* (2013.01); *Y02E 60/527* (2013.01); *Y02P 20/133* (2015.11); *Y02P 20/135* (2015.11); *Y02P 70/56* (2015.11)

(58) Field of Classification Search
None
See application file for complete search history.

(56) References Cited

U.S. PATENT DOCUMENTS

| 5,443,706 A | 8/1995 | Kuroda et al. |
| 2004/0241771 A1 | 12/2004 | Zeikus et al. |
| 2008/0305540 A1 | 12/2008 | Hickey et al. |
| 2009/0191593 A1 | 7/2009 | Burk et al. |
| 2009/0317882 A1 | 12/2009 | Cheng et al. |
| 2011/0315560 A1 | 12/2011 | Rabaey et al. |

OTHER PUBLICATIONS

International Search Report dated Aug. 26, 2011.
Written Opinion of the International Searching Authority dated Aug. 26, 2011.
Xiaoxin Cao et al., A completely anoxic microbial fuel cell using a photo-biocathode for cathodic carbon dioxide reduction, Energy Environ. Sci., pp. 498-501, published Feb. 23, 2009.
Kelvin B. Gregory et al., Graphite electrodes as electron donors for anaerobic respiration, Environmental Microbiology (2004) 6 (6), 596-604.
Ho II Park et al., Nitrate reduction using an electrode as direct electron donor in a biofilm-electrode reactor, Process Biochemistry 40 (2005) 3383-3388.
Kelvin B. Gregory et al., Remediation and Recovery of Uranium from Contaminated Subsurface Environments with Electrodes, Environ. Sci. Technol. 2005, 39, 8943-8947, Published on Web Oct. 13, 2005.
Derek R Lovley, Microbial fuel cells: novel microbial physiologies and engineering approaches, Current Opinion in Biotechnology 2006, 17:327-332 (May 5, 2006).
Derek R. Lovley, Bug juice: harvesting electricity with microorganisms, Nature Reviews Microbiology, vol. 4, pp. 497-508, Jul. 2006.
Bruce E. Logan, Microbial Fuel Cells: Methodology and Technology, Environmental Science & Technology vol. 40, No. 17, pp. 5181-5192, 2006, published on web Jul. 14, 2006.
Sarah M. Strycharz et al., Graphite Electrode as a Sole Electron Donor for Reductive Dechlorination of Tetrachlorethene by Geobacter lovleyi, Applied and Environmental Microbiology, vol. 74, No. 19, p. 5943-5947, 2008 (Published ahead of print on Jul. 25, 2008).
Derek R Lovley, The microbe electric: conversion of organic matter to electricity, Current Opinion in Biotechnology 2008, 19:564-571, (Available online Nov. 13, 2008).
Shaoan Cheng et al., Direct Biological Conversion of Electrical Current into Methane by Electromethanogenesis, Environ. Sci. Technol. 2009, 43, 3953-3958 (Published on Web Mar. 26, 2009).
Du, A state of the art review of microbial fuel celis, May 2007, Biotechnology Advances, 25, 464-482.

(Continued)

*Primary Examiner* — Taeyoon Kim
*Assistant Examiner* — Srikanth Patury
(74) *Attorney, Agent, or Firm* — Milstein Zhang & Wu LLC; Joseph B. Milstein

(57) ABSTRACT

The invention provides systems and methods for generating organic compounds using carbon dioxide as a source of carbon and electrical current as an energy source. In one embodiment, a reaction cell is provided having a cathode electrode and an anode electrode that are connected to a source of electrical power, and which are separated by a permeable membrane. A biological film is provided on the cathode. The biological film comprises a bacterium that can accept electrons and that can convert carbon dioxide to a carbon-bearing compound and water in a cathode half-reaction. At the anode, water is decomposed to free molecular oxygen and solvated protons in an anode half-reaction. The half-reactions are driven by the application of electrical current from an external source. Compounds that have been produced include acetate, butanol, 2-oxobutyrate, propanol, ethanol, and formate.

18 Claims, 20 Drawing Sheets

(56) References Cited

OTHER PUBLICATIONS van Kasteren et al., Bio-ethanol from bio-syngas, Technische Universiteit Eindhoven (TUfe), Dec. 5, 2005, 53 pages.
Paul et al., Genome Sequence of the Solvent-Producing Bacterium Clostridium carboxidivorans Strain P7TV, Journal of Bacteriology, vol. 192, No. 20, Oct. 2010, p. 5554-5555 (Published ahead of print on Aug. 20, 2010).
Clauwaert et al., Minimizing losses in bio-electrochemical systems: the road to applications, Appl. Microbiol. Biotechnol., 79:901-913, 2008.
Rabaey et al., Microbial electrosynthesis—revisiting the electrical route for microbial production, Nature Reviews Microbiology, vol. 8, p. 706-716, Oct. 2010.

n-butanol isobutanol sec-butanol tert-butanol

MICROBIAL PRODUCTION OF MULTI-CARBON CHEMICALS AND FUELS FROM WATER AND CARBON DIOXIDE USING ELECTRIC CURRENT

CROSS-REFERENCE TO RELATED APPLICATIONS

This application is a divisional application of U.S. patent application Ser. No. 13/514,378, filed Jun. 7, 2012, now U.S. Pat. No. 9,175,408, issued Nov. 3, 2015, which application is a national application under 35 U.S.C. 371 of PCT/US10/61690, filed Dec. 22, 2010, which application in turn claimed priority to and the benefit of then U.S. provisional patent application Ser. No. 61/289,349 filed Dec. 22, 2009, each of which applications is incorporated herein by reference in its entirety.

STATEMENT REGARDING FEDERALLY FUNDED RESEARCH OR DEVELOPMENT

The U.S. Government has certain rights in this invention pursuant to Cooperative Agreement DE-FC02-02ER63446 awarded by the Office of Science (BER), U.S Department of Energy, and Agreement No. DE-AR0000087 awarded by ARPA-E.

FIELD OF THE INVENTION

The invention relates to chemical reactions in general and particularly to systems and methods that employ biological systems that allow the generation of carbon-bearing compounds using carbon dioxide as a source under an electrical stimulus.

BACKGROUND OF THE INVENTION

Various chemicals and fuels are manufactured using laboratory synthesis or are extracted from natural sources. Examples include pharmaceutical precursors and organic compounds, such as ethanol and other alcohols, fatty acids, sugars, hydrocarbons, acid esters, citric acids, essential oils, ethyl chloride, formaldehyde, glycerin, lactic acid, monosodium glutamate (MSG), peroxides, saccharin, stearic acid, and vinyl acetate. The economic value of such products manufactured in the U.S. is measured in the billions of dollars annually. Naturally occurring chemicals and fuels are produced in natural systems that rely on photosynthesis. Processing biomass through fermentation to produce chemicals or fuels, the most common example being ethanol, is also well known.

Certain microorganisms have been shown to interact electrochemically with electrodes without requiring molecules that shuttle electrons between the electrodes and the microorganisms (see Lovley, D. R. 2006. Bug juice: harvesting electricity with microorganisms. Nature Rev. Microbiol. 4:497-508 and Lovley, D. R. 2008. The microbe electric: conversion of organic matter to electricity. Curr. Opinion Biotechnol. 19:564-571). In some instances microorganisms, such as *Geobacter* species, have the ability to oxidize organic compounds to carbon dioxide with electron transfer to electrodes. (see Bond, D. R., D. E. Holmes, L. M. Tender, and D. R. Lovley. 2002. Electrode-reducing microorganisms that harvest energy from marine sediments. Science 295:483-485. Bond, D. R., and D. R. Lovley. 2003. Electricity production by *Geobacter sulfurreducens* attached to electrodes. Appl. Environ. Microbiol. 69:1548-1555. Chaudhuri, S. K., and D. R. Lovley. 2003. Electricity generation by direct oxidation of glucose in mediatorless microbial fuel cells. Nat. Biotechnol. 21:1229-1232). Such microorganisms can produce electrical current in microbial fuel cells.

FIG. 1 is a schematic diagram that illustrates the operation of a microbial fuel cell of the prior art. Microbial Fuel Cells are described in U.S. Patent Application Publication 2008/0286624 A1, published Nov. 20, 2008, the disclosure of which is incorporated herein by reference in its entirety. The article entitled "Microbial fuel cells: novel microbial physiologies and engineering approaches," by D R Lovley, in Current Opinion in Biotechnology Volume 17, Issue 3, June 2006, Pages 327-332, describes Benthic Unattended Generators or BUGs, which are microbial fuel cells (MFCs) that can harvest electricity from the organic matter in aquatic sediments by oxidizing the organic matter and having the electricity so produced flow from the anode of the fuel cells through a load external to the fuel cell cathode. That article explains that BUGs consist of an anode buried in anoxic marine sediments connected to a cathode suspended in the overlying aerobic water that provides the free (or molecular) oxygen needed to operate the fuel cell.

Conventional microbial fuel cells (MFCs) operate in the following manner: a biofilm of electricigenic bacteria (e.g. *Geobacter, Shewanella*, etc) forms (or is provided) on the anode. The bacteria metabolize organic compounds such as acetate, with the generation of electrons and protons. The bacteria directly transfer electrons to the anode. The electrons flow through an external circuit to the cathode, thereby generating current. The protons flow though the medium, pass through a selectively permeable membrane to the cathodic chamber, where oxygen is reduced at the cathode, and combines with protons to form water.

In some cases an electrode has been used as an electron donor. FIG. 2 is an illustrative schematic diagram that shows the configuration of a prior art cell that uses an electrode to supply electrons for reduction of chemicals. A primary study of this was in *Geobacter sulfurreducens*, where an electrode served as electron donor, the electron acceptor was fumarate, and the reduced compound was succinate (Gregory, Kelvin B.; Bond, Daniel R.; Lovley, Derek R., Graphite electrodes as electron donors for anaerobic respiration, Environmental Microbiology. 6(6):596-604, June 2004). Fumarate, also called fumaric acid, or trans-butenedioic acid, is a dicarboxylic acid with the formula $HO_2CCH=CHCO_2H$. Succinate, also called succinic acid, or butanedioic acid, is a dicarboxylic acid with the formula $HO_2CCH_2-CH_2CO_2H$, which is produced by hydrogenating the double carbon-carbon bond in fumaric acid.

Other studies, primarily with *Geobacter*, followed using the electrode as donor for nitrate reduction to nitrite (Gregory, Kelvin B.; Bond, Daniel R.; Lovley, Derek R., Graphite electrodes as electron donors for anaerobic respiration, Environmental Microbiology. 6(6):596-604, June 2004), uranium (VI) reduction to U(IV) (Gregory, K. B., and D. R. Lovley 2005. Remediation and recovery of uranium from contaminated subsurface environments with electrodes. Environ Sci Technol 39(22):8943-8947); and dechlorination of chlorinated organic solvents in groundwater (Sarah M. Strycharz, Trevor L. Woodard, Jessica P. Johnson, Kelly P. Nevin, Robert A. Sanford, Frank E. Loffler, and Derek R. Lovley, Graphite Electrode as a Sole Electron Donor for Reductive Dechlorination of Tetrachlorethene by Geobacter lovleyi, Applied and Environmental Microbiology, October 2008, p. 5943-5947, Vol. 74, No. 19).

In a paper by Shaoan Cheng, Defeng Xing, Douglas F. Call, and Bruce E. Logan, entitled "Direct Biological Conversion of Electrical Current into Methane by Electromethanogenesis" that was published online on Mar. 26, 2009 (http://pubs.acs.org| doi: 10.1021/es803531g), the authors stated that ...we demonstrate that methane can directly be produced using a biocathode containing methanogens in electrochemical systems (abiotic anode) or microbial electrolysis cells (MECs; biotic anode) by a process called electromethanogenesis. . . .

Renewable biomethane is typically produced by methanogens from a few substrates such as acetate, formate, and biohydrogen gas in anaerobic digesters. Based on thermodynamic calculations, methane could also be produced electrochemically through carbon dioxide reduction at a voltage of 0.169 V under standard conditions, or −0.244 V under more biologically relevant conditions at a pH=7, by the reaction $$CO_2 + 8H^+ 8e^- \rightarrow CH_4 + 2H_2O \qquad \text{Rxn(1)}$$

This suggests that methane could be produced without an organic fuel, at about the same potential needed for hydrogen production with an organic fuel (such as acetate)".

In particular, it is apparent from this passage that these scientists consider acetate (or acetic acid) to be a fuel to be consumed, and do not consider acetate (or acetic acid) to be a product that one might make in the reaction system that they describe. In fact, the electrons supplied for methane production at the cathode in this system were derived from the oxidation of acetate at the anode. In addition, this paper does not describe the production of any chemical other than methane (i.e., it does not describe the production of any chemical having a plurality of carbon atoms therein), nor does it describe a reaction that generates hydrocarbons and molecular oxygen as products. Furthermore, the reduction of carbon dioxide to methane, a compound with the same number of carbons as the starting material, is analogous to the previously described microbial reduction of fumarate to succinate with an electrode serving as the electron donor. Therefore, the study by Cheng and co-workers did not foresee the possibility of reducing carbon dioxide to form covalent carbon-carbon bonds to produce multi-carbon products.

For compounds that have a high cost of production, it would be advantageous to have a biologically-based production system that is more energy-efficient and economical than current methods of manufacturing these chemicals.

There is a need for systems and methods that can produce hydrocarbon chemicals and molecular oxygen directly using as reagents water and carbon dioxide in analogy to photosynthesis in plants.

SUMMARY OF THE INVENTION

According to one aspect, the invention features an apparatus for generating a carbonaceous chemical wherein carbon dioxide is a source of carbon. The apparatus comprises a reaction vessel having an anode electrode and a cathode electrode disposed therein, the anode electrode having at least one surface and an anode electrical contact terminal, the cathode electrode having at least one surface and a cathode electrical contact terminal, the cathode electrode having a film of biologically active material adjacent to at least one surface of the cathode electrode and in electrical communication therewith, the reaction vessel configured to contain a working fluid having mobile ions therein; a reaction medium in contact with the cathode electrode and the anode electrode, the reaction medium configured to contain carbon dioxide as a source of carbon and to contain a substance configured to be oxidized; a source of electrical energy, the source of electrical energy electrically connected to the cathode electrical contact terminal and to the anode electrical contact terminal; and a source of carbon dioxide configured to provide carbon dioxide to the film of biologically active material adjacent to at least one surface of the cathode electrode by way of the reaction medium.

In one embodiment, the reaction vessel has a first chamber and a second chamber, the first chamber and the second chamber each configured to contain a working fluid having mobile ions therein, the first chamber and the second chamber separated by a membrane permeable to at least a selected ionic species, the anode electrode disposed in one of the first chamber and the second chamber and the cathode electrode disposed in the other of the first chamber and the second chamber.

In another embodiment, the film of biologically active material comprises an organism that is able to generate a carbonaceous chemical having at least two carbon atoms using carbon dioxide as a source of carbon.

In yet another embodiment, the carbonaceous chemical comprises carbon, hydrogen and oxygen.

In still another embodiment, the carbonaceous chemical comprises at least two carbon atoms.

In a further embodiment, the working fluid having mobile ions therein is a source of a chemical species configured to be oxidized.

In yet a further embodiment, the apparatus further comprises a control module configured to control a selected one of an electrical potential applied between the cathode electrode and the anode electrode, and an electrical current caused to flow between the cathode electrode and the anode electrode.

In an additional embodiment, the apparatus further comprises a third electrode having a third electrical contact terminal in electrical communication with the control module, the third electrode configured to provide a reference potential relative to a selected one of the cathode electrode and the anode electrode.

In one more embodiment, at least one of the cathode electrical contact terminal and the anode electrical contact terminal is external to the vessel.

In still a further embodiment, the source of electrical energy is a renewable energy source.

In one embodiment, the renewable energy source is selected from the group consisting of a solar cell, solar thermal energy, wind energy, hydroelectricity, geothermal and a biomass-fired electrical generator.

In another embodiment, the solar cell is selected from the group consisting of photovoltaic solar cells and photoelectrochemical solar cells.

In yet another embodiment, the source of carbon dioxide is selected from the group consisting of carbon dioxide in an effluent from a combustion process of coal, petroleum, methane, natural gas, biomass, organic carbon, an industrial process that releases carbon dioxide, carbon dioxide from geothermal sources, atmospheric $CO_2$, $CO_2$ from dry ice, $CO_2$ from carbonate minerals, $CO_2$ from carbonic acid ($H_2CO_3$), and $CO_2$ sequestered from the atmosphere.

In still another embodiment, the apparatus further comprises a source of ionic hydrogen and a source of ionic oxygen.

In a further embodiment, the source of ionic hydrogen and the source of ionic oxygen is water.

In yet a further embodiment, at least one of the cathode electrode and the anode electrode comprises a material selected from the group consisting of carbon paper, carbon cloth, carbon felt, carbon wool, carbon foam, graphite, porous graphite, graphite powder, graphene, carbon nanotubes, electrospun carbon fibers, a conductive polymer, platinum, palladium, titanium, gold, silver, nickel, copper, tin, iron, cobalt, tungsten, stainless steel, and combinations thereof.

According to one aspect, the invention features a method of generating a carbonaceous chemical wherein carbon dioxide is a source of carbon. The method comprises the steps of providing a reaction vessel having an anode electrode and a cathode electrode disposed therein, the anode electrode having at least one surface and an anode electrical contact terminal, the cathode electrode having at least one surface and a cathode electrical contact terminal, the cathode electrode having a film of biologically active material adjacent to at least one surface of the cathode electrode and in electrical communication therewith, the reaction vessel configured to contain a working fluid having mobile ions therein; providing a reaction medium in contact with the cathode electrode and the anode electrode, the reaction medium containing carbon dioxide as a source of carbon and to contain a substance configured to be oxidized; providing a source of electrical energy, the source of electrical energy electrically connected to the cathode electrical contact terminal and to the anode electrical contact terminal; and providing a source of carbon dioxide configured to provide carbon dioxide to the film of biologically active material adjacent the at least one surface of the cathode electrode by way of the reaction medium; and operating the source of electrical power to provide electrons to the cathode and to extract electrons from the anode; whereby a carbonaceous chemical containing at least two carbon atoms is generated in a vicinity of the cathode having the biofilm in electrical communication therewith.

In one embodiment, a net chemical reaction that occurs is described by the equation $2\ CO_2 + 2\ H_2O \rightarrow CH_3COOH + 2\ O_2$.

In another embodiment, the a net chemical reaction that occurs is described by the equation $4\ CO_2 + 5\ H_2O \rightarrow \text{Butanol}\ (C_4H_{10}O) + 6\ O_2$.

In yet another embodiment, a net chemical reaction that occurs is described by the equation $M\ CO_2 + N\ H_2O \rightarrow C_M H_Y O_Z + P\ O_2$ where M, N and P are non-negative numbers and Y=2N, and Z=2M+N−2P. Compounds that have been produced include acetate, butanol, 2-oxobutyrate, propanol, ethanol, and formate.

In still another embodiment, the reaction vessel has a first chamber and a second chamber, the first chamber and the second chamber each configured to contain a working fluid having mobile ions therein, the first chamber and the second chamber separated by a membrane permeable to at least a selected ionic species, the anode electrode disposed in one of the first chamber and the second chamber and the cathode electrode disposed in the other of the first chamber and the second chamber.

In a further embodiment, the reaction vessel further comprises a semi-permeable membrane.

In yet a further embodiment, the substance configured to be oxidized contains oxygen.

In an additional embodiment, the biofilm comprises a bacterium of the genus *Geobacter*.

In one more embodiment, the biofilm comprises a bacterium of a genus selected from the group of consisting of the genera *Sporomusa, Clostridium* and *Moorella*.

In still a further embodiment, the biofilm comprises an acetogenic bacterium.

In one embodiment, the biofilm comprises microorganisms derived from plant rhizosphere.

In another embodiment, the biofilm comprises microorganisms derived from a source selected from the group consisting of contaminated water, soil, waste streams, and sewage sludge.

In yet another embodiment, the chemical containing at least two carbon atoms is acetyl-CoA.

In still another embodiment, the source of carbon dioxide is selected from the group consisting of carbon dioxide in an effluent from a combustion process of coal, petroleum, methane, natural gas, biomass, organic carbon, an industrial process that releases carbon dioxide, carbon dioxide from geothermal sources, atmospheric $CO_2$, $CO_2$ from dry ice, $CO_2$ from carbonate minerals, $CO_2$ from carbonic acid ($H_2CO_3$), and $CO_2$ sequestered from the atmosphere.

In an additional embodiment, the biofilm mediates the production of the chemical containing at least two carbon atoms using a Wood-Ljungdahl pathway.

In one more embodiment, the biofilm mediates the production of the chemical containing at least two carbon atoms using a reverse tricarboxylic acid pathway.

In still a further embodiment, the biofilm mediates the production of the chemical containing at least two carbon atoms using a 4-hydroxybutryate pathway.

In one embodiment, the reaction vessel comprises a semi-permeable membrane. However, for a large enough vessel, or one designed correctly, for example in the form of the laboratory "U" tube setup for electrolytic decomposition of water, such that the reaction products generated at one electrode are sufficiently separated from the reaction products generated at the other electrode, a membrane may not be needed.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Figure 1:
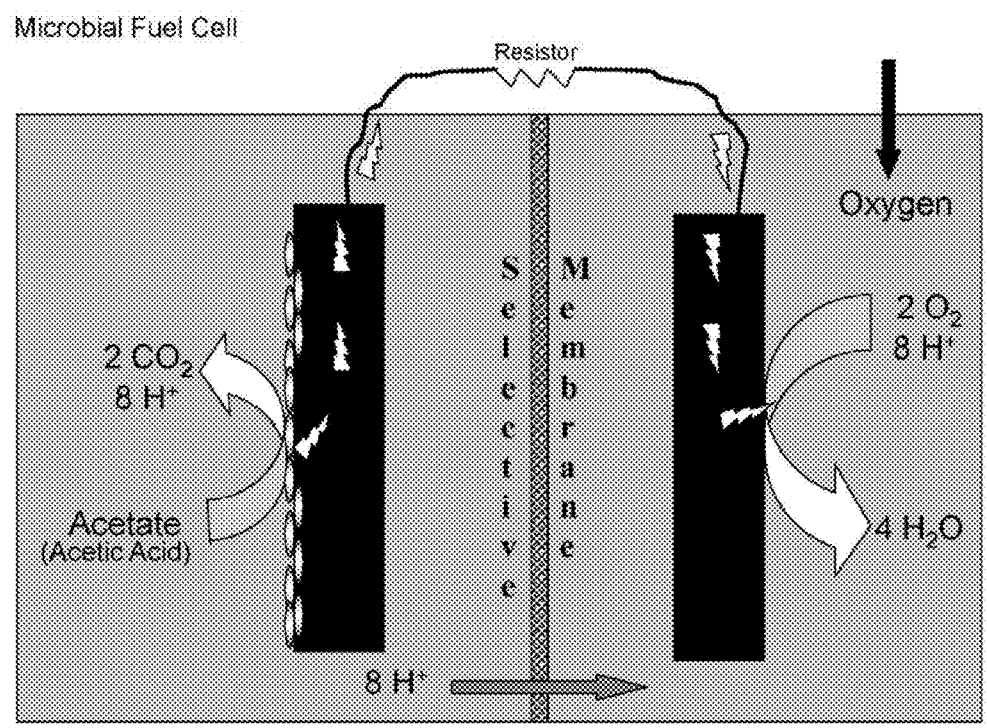
FIG. 1 is a schematic diagram that illustrates the operation of an MFC of the prior art.

The discovery of electrotrophs, microorganisms that can directly accept electrons from electrodes for the reduction of terminal electron acceptors, has spurred the investigation of a wide range of potential applications. To date, only a handful of pure cultures have been shown to be capable of electrotrophy, but this process has also been inferred in many studies with undefined consortia. Potential electron acceptors include: carbon dioxide, nitrate, metals, chlorinated compounds, organic acids, protons and oxygen. Direct electron transfer from electrodes to cells has many advantages over indirect electrical stimulation of microbial metabolism via electron shuttles or hydrogen production. Supplying electrons with electrodes for the bioremediation of chlorinated compounds, nitrate or toxic metals may be preferable to adding organic electron donors or hydrogen to the subsurface or bioreactors.

We propose the term "microbial electrosynthesis" for the reduction of carbon dioxide to multicarbon compounds with electrons donated from an electrode as the electron donor. Microbial electrosynthesis differs significantly from photosynthesis in that carbon and electron flow is directed primarily to the formation of extracellular products, rather than biomass. Biomass typically requires extensive additional processing for chemical or fuel production. Coupling photovoltaic technology with microbial electrosynthesis represents a novel photosynthesis strategy that avoids many of the drawbacks of biomass-based strategies for the production of transportation fuels and other organic chemicals. The mechanisms for direct electron transfer from electrodes to microorganisms warrant further investigation in order to optimize envisioned applications.

Engineered microbial processes, such as the production of fuels and other chemicals as well as bioremediation, have traditionally relied on biomass-based organic feedstocks as the electron donor. Potential advantages of microbial electrosynthesis over biomass-based strategies for the production of fuels and chemicals include: the 100-fold higher efficiency of photovolatics in harvesting solar energy; eliminating the need for arable land; avoiding the environmental degradation (such as introduction of excess nutrients and other pollutants) associated with intensive agriculture; and the direct production of desired products. Like photovoltaics, other major renewable forms of energy such as wind, hydro and geothermal can also produce electricity. Therefore, the possibility of powering beneficial microbial processes with electricity is becoming increasingly attractive. As detailed below, this may be most effectively accomplished by providing microorganisms with electrons via direct electron transfer from electrodes, coupled to the microbial reduction of various electron acceptors.

Microorganisms capable of directly accepting electrons from electrodes have been referred to colloquially as electrode-oxidizing bacteria, just as microorganisms are referred to iron-oxidizing, sulfur-oxidizing or methane-oxidizing microbes. A more formal designation may be electrotrophs in accordance with the standard parlance of chemotrophs that oxidize chemical compounds in their environments (organotrophs oxidize organic compounds; lithotrophs oxidize inorganics) and phototrophs.

A recent review by D. R. Lovley (Powering microbes with electricity: direct electron transfer from electrodes to microbes, Article first published online: 16 Sep. 2010, DOI: 10.1111/j.1758-2229.2010.00211.x) summarizes current knowledge on how electrons can be directly transferred from electrodes to microorganisms and the potential practical applications of this novel form of microbial respiration in bioremediation, bioenergy, and chemical production.

Another recent paper (Nevin, K. P., T. L. Woodard, A. E. Franks, Z. M. Summers, and D. R. Lovley. 2010. Microbial electrosynthesis: feeding microbes electricity to convert carbon dioxide and water to multicarbon extracellular organic compounds. mBio 1(2):e00103-10. doi:10.1128/mBio.00103-10) describes the first demonstration of microbial production of chemicals (including chemicals having more than one carbon atom therein) from carbon dioxide and water using power provided by an imposed electrical current. This system operates in the reverse manner as compared to MFCs. This system is useful to produce chemicals, for example commodity chemicals such as acetic acid, that are useful in their own right, and also serve as chemical precursors for the production of many other commodity and fine chemicals which are well known and have recognized uses. For example, DPM is a defined medium for penicillin biosynthesis that contains acetic acid as a constituent. Acetic acid is used to make vinyl acetate monomer. Vinyl acetate can be polymerized to polyvinyl acetate or to other polymers, which are applied in paints and adhesives. Glacial acetic acid is an excellent polar protic solvent that is frequently used as a solvent for recrystallization to purify organic compounds.

Various inorganic salts are produced from acetic acid. By way of example, sodium acetate is used in the textile industry and as a food preservative; copper(II) acetate is used as a pigment and a fungicide; aluminum acetate and iron(II) acetate are used as mordants for dyes; palladium(II) acetate is used as a catalyst for organic coupling reactions such as the Heck reaction; and silver acetate is used as a pesticide.

The inventors have demonstrated a new application that uses the microbial fuel cell structure, but that operates in the reverse sense, e.g., rather than generating electricity, they use electricity provided from an external source as the energy source to remove electrons from water and reduce $CO_2$ as an electron acceptor. These systems are able to manipulate bacteria into producing organic compounds, effectively reversing the usual MFC electricity flow direction, and generating organic compounds and oxygen rather than oxidizing organic compounds and consuming free oxygen.

The inventors have reversed the MFC process to enable a very powerful and novel technology that can sequester carbon (in the form of $CO_2$) as organic compounds (e.g. acetic acid or acetate). Production of acetate is the reduction of the conception of the invention, and proves that one is able to produce known compounds, and a range of as-yet unidentified organic compounds. This is accomplished by providing a biofilm of the acetogenic bacterium *Sporomusa ovata*, situated on an electrode with a stream of electrons and $CO_2$. As explained below, other acetogenic bacteria in the genus *Sporomusa*, as well as acetogenic bacteria in the genera *Clostridium* and *Morella*, perform in a similar manner. The bacteria utilize (or consume) electrons and $CO_2$ to synthesize acetic acid and other organic compounds. It is expected that this approach is useful as a method for producing chemicals containing a plurality of carbon atoms, while employing electricity produced by solar cells (or other renewable energy source of electricity) to power a reaction system to sequester $CO_2$ and synthesize one or more desired organic compounds. In more advanced embodiments, it is expected that acetogenic bacteria can be engineered to selectively produce fine chemicals/organic compounds of commercial value (e.g., fuel-grade compounds).

In some preferred embodiments, the present invention provides a system to produce multi-carbon organic compounds from carbon dioxide and water. The system includes an electrical power supply, an anodic electrode capable of extracting electrons from water, a cathodic electrode, and a microorganism that can use electrons derived from the cathodic electrode to fix carbon dioxide into organic compounds. In one embodiment, carbon dioxide is fixed to produce acetate. This is accomplished with acetogenic bacteria, as is described in more detail herein below. There is a wide diversity of acetogenic bacteria. It is expected that many of these bacteria are also capable of fixing carbon dioxide to produce acetate or other compounds containing at least two carbon atoms. Other organic products that have been documented to be produced include: 2-oxobutyric acid, ethanol, propanol, butanol, and formate.

Organic acids are also produced from carbon dioxide with a biofilm of *Geobacter metallireducens* on the cathode. Organic acids documented to be produced include: acetate, formate, ethanol, butanol, 2-oxobutyric acid and other as yet unidentified organic acids.

The ability to accept electrons from an electrode is a hallmark feature of *Geobacter* species. It is expected that a wide diversity of other *Geobacter* species can fix carbon dioxide into organic acids or other compounds in this manner.

We have previously shown that *Anaeromyxobacter* can accept electrons from an electrode. It is expected that *Anaeromyxobacter* may be capable of carbon dioxide fixation according to the principles enunciated herein.

We have demonstrated that there are microorganisms in sewage sludge and the plant rhizosphere that can also make acetate and other organic acids in reaction cells as described herein.

The production of documented products proceeds through acetyl-CoA (CAS number 72-89-9) as an intermediate. It is well known that microorganisms contain enzymes that can produce a wide diversity of useful products with acetyl-CoA as the starting product. Therefore, it is envisioned that these products can also be produced in the microbial reductive cell through expression of the appropriate genes. A wide variety of organic compounds that can be produced, which can include but are not limited to alcohols, amino acids, sugars, fatty acids, aromatic compounds, diols, and others.

Potential sources of carbon dioxide include but are not limited to carbon dioxide from combustion of coal, petroleum, methane or natural gas, biomass, or other sources of organic carbon, carbon dioxide from processing of aluminum and other industrial processes that release carbon dioxide, carbon dioxide from geothermal sources, and carbon dioxide from the burning of organic carbon. Other sources of carbon dioxide include but are not limited to $CO_2$ from the atmosphere, $CO_2$ from dry ice, $CO_2$ from carbonate minerals, $CO_2$ from carbonic acid ($H_2CO_3$), and $CO_2$ sequestered from the atmosphere. In general, any convenient source of $CO_2$ can be used.

Carbon dioxide fixation that occurs in microorganisms such as acetogens is believed to occur via the Wood-Ljungdahl pathway. Carbon dioxide fixation that occurs in microorganisms such as *Geobacter* species is believed to occur via the reverse tricarboxylic acid pathway or the 4-hydroxybutyrate pathway It is believed that the generation of organic compounds, including compounds having more than one carbon atom, using this combination of electricity, $CO_2$ and bacteria in a man-made reaction cell is a novel process.

In this invention one uses a similar electrode system as is illustrated in FIG. 1 in reverse (e.g., donor) mode. Instead of using fumarate, uranium or nitrate as electron acceptor, carbon dioxide is the electron acceptor with the production of chemicals containing two or more carbon atoms as the final product. Acetogenic bacteria perform this process in nature (production of acetic acid or acetate), with hydrogen as the electron donor. In the present system, hydrogen is replaced with the electrode system. It is possible to run this process to produce chemicals directly from the energy of the sun, (e.g., without the need for photosynthesis). In that sense, this process could be analogized to photosynthesis. It is expected that the chemicals produced will depend on the genetics of the acetogen used. *Sporomusa, Chlostridium, Geobacter,* and *Morella* species and mixed communities of bacteria have been tested and have been demonstrated to produce acetic acid, though it is likely that many acetogenic bacteria are capable of this type of metabolism. A listing of inocula that have been tried and the currents that were observed is presented in Table I. Results obtained to date indicate that a wide variety of chemical are produced. FIGS. 4, 5A, 5B, 6B, 11A, 11B, 13, 15, and 16 show results of lab experiments, in which increasing quantities of acetate and other organic acids are produced as more current is drawn by the biofilms on the electrodes. High performance liquid chromatograph data shows that other chemicals that have yet to be identified are also produced during this process.

TABLE I

| Type of Inoculum | Max current draw (mA) |
|---|---|
| *Sporomusa ovata* | −1.8 |
| *Sporomusa sphaeroides* | −2.1 |
| *Sporomusa silvacetica* | −0.5 |
| *Clostridium aceticum* | −1.25 |
| *Clostridium ljungdahlii* | −2.0 |
| *Moorella thermoacetica* | −0.5 |
| *Geobacter metallireducens* | −1.0 |
| Anaerobic Digester Sludge | −1.6 |
| Soybean Rhizosphere | −1.0 |
| Green bean Rhizosphere | −0.5 |

Media types used to grow and to operate the methods of the invention are listed in Table IA below, and the media are described in an Appendix.

TABLE IA

| Type of Inoculum | Media | Growth conditions |
|---|---|---|
| *Sporomusa* species | DSMZ 311 | For acetogenic growth omit Casitone and Betaine. |
| *Clostridium ljungdahlii* | DSMZ 879 | For acetogenic growth omit glucose. |
| *Clostridium aceticum* | DSMZ 135 | For acetogenic growth omit Fructose and Resazurin |
| *Moorella thermoacetica* | DSMZ 60 | For acetogenic growth omit glucose. |
| *Geobacter* and enrichments | DSMZ 826 | For enrichments and acetogenic growth omit fumarate, acetate and resazaurin. |

Table II is a listing of bacteria that have been used to produce acetic acid and that drew current on the electrode during the acetic acid or acetate production, along with a listing of the media used and the temperature of operation.

TABLE II

| Type of Innoculum | Medium | Temperature |
|---|---|---|
| *Clostridium aceticum* (DSMZ1496) | DSMZ media #135 | 25° C. |
| *Clostridium ljungdahii* (DSMZ 13528) | Freshwater media | 37° C. |
| *Geobacter metallireducens* (lab collection, DSMZ 7210) | Freshwater media | 25° C. |
| *Geobacter metallireducens* pRG5: dcuB (lab collection) | Freshwater media | 25° C. |
| *Moorella thermoacetica* (DSMZ 521) | DSMZ media #60 | 37° C. |
| *Sporomusa ovata* (DSMZ 2662) | DSMZ media #311 | 25° C. |
| *Sporomusa sphaeroides* (DSMZ 2875) | DSMZ media #311 | 25° C. |
| *Sporomusa silvacetica* (DSMZ 10669) | DSMZ media #311 | 25° C. |
| Sewage Sludge | Freshwater media | 37° C. |
| SoyBean Rhizosphere | Freshwater media | 25° C. |

We can describe a first embodiment of the chemistry that occurs in the systems and processes described herein, which is expressed by the following two half-reactions:

The half-reaction at the cathode is:

$$2CO_2 + 8H^+ + 8e^- \rightarrow CH_3COOH + 2H_2O \qquad \text{Rxn(2)}$$

The half-reaction at the anode is:

$$2H_2O \rightarrow 4H^+ + 4e^- + O_2 \qquad \text{Rxn (3)}$$

For charge balance, we can double Rxn (3):

$$4H_2O \rightarrow 8H^+ + 8e^- + 2O_2 \qquad \text{Rxn (3')}$$

Summing Rxn (2) and Rxn (3') and canceling common terms on each side of the reaction gives a net reaction of:

$$2CO_2 + 2H_2O \rightarrow CH_3COOH + 2O_2 \qquad \text{Rxn (4)}$$

Rxn (4) describes the consumption of $CO_2$ at the cathode and $H_2O$ at the anode to produce $CH_3COOH$ (acetic acid) at the cathode and $O_2$ at the anode. This reaction is similar to the equation that describes the chemical changes that occur during photosynthesis, in which 6 water molecules and 6 carbon dioxide molecules are reacted to produce glucose (sugar) and 6 molecules of oxygen:

$$6CO_2 + 6H_2O \rightarrow C_6H_{12}O_6 + 6O_2 \qquad \text{(Photosynthesis Rxn)}$$

We further describe another embodiment in which a different compound, 2 oxobutyric acid containing four carbon atoms, is produced. 2-oxobutyric acid has the chemical formula $(CH_3)$—$CH_2$—$CO$—$COOH$, or $C_4H_6O_3$ The net reaction is given by $$4CO_2+3H_2O \rightarrow C_4H_6O_3+4O_2 \qquad \text{Rxn (5)}$$

which reaction can be understood as the sum of 4 times Rxn (3) at the anode:

$$8H_2O \rightarrow 16H^+ + 16e^- + 4O_2 \qquad 4\times \text{Rxn (3)}$$

and Rxn (6) at the cathode:

$$4CO_2+16H^++16e^- \rightarrow CH_3CH_2COCOOH+5H_2O \qquad \text{Rxn (6)}$$

A strain of *Clostridium ljungdahii*, which has had genes added for butanol production, produced butanol in a similar manner.

To the extent that the acetic acid, 2 oxobutyric acid, butanol, or other organic compound that is produced is generated using sunlight (with conversion of sunlight to electricity as an intermediate step), Rxn (4), Rxn (6), or similar reactions can be considered to be analogous to the photosynthesis reaction in that water and carbon dioxide are converted to a compound that can be oxidized (or burned), along with a co-product, free molecular oxygen. Just as green plants generate carbohydrates and oxygen by photosynthesis, and consume carbon dioxide in so doing, the technologies provided by the systems and methods of the invention can be considered "green" or environmentally friendly.

The reactions described herein using $CO_2$ as a carbon source change (specifically, increase) the number of carbons in the product molecule from the number in the reagent molecules, in which the change represents chemical synthesis, and is not simply a reductive reaction such as converting fumarate to succinate or carbon dioxide to methane in which the number of carbons present in the carbon backbone is unchanged.

Making carbohydrates from $CO_2$ is not well-known synthetic chemistry as far as the inventors are aware, but is known in nature. Humankind has been puzzling for years over exactly how "Mother Nature" performs the miracle of photosynthesis. The man-made generation of chemical compounds containing a plurality of carbon atoms, and chemical compounds containing carbon, hydrogen and oxygen, from a carbon source such as carbon dioxide that contains only one carbon satisfies a long felt but unmet need. The technology described herein provides systems and methods that convert one substance into another substance using known materials to obtain an unexpected result. In particular, the systems and methods of the present disclosure can be powered using renewable energy sources, and can consume waste $CO_2$. The reactions also consume water and generate molecular oxygen as a product.

Description of the Reaction Apparatus

Figure 2:
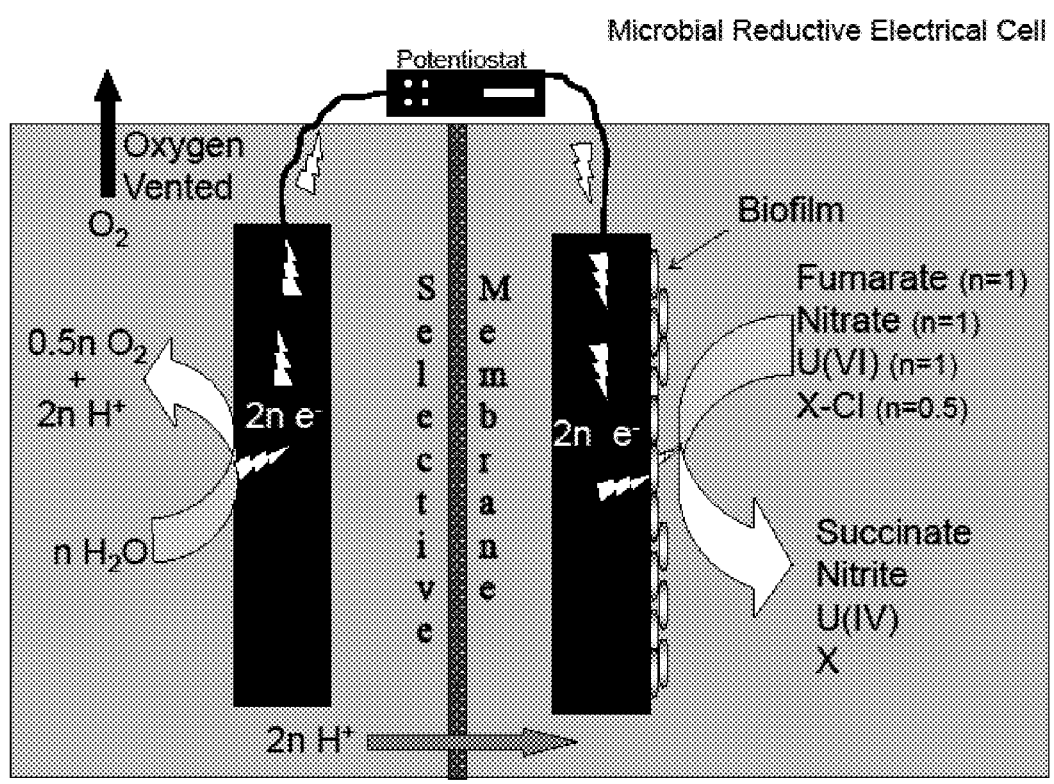
FIG. 2 is an illustrative schematic diagram that shows the configuration of a cell that uses an electrode to supply electrons for reduction of chemicals. The reduction of various electron acceptors have been documented in pure culture. Water is the electron donor of choice at the anode for many applications, but electrons may be supplied with other strategies, such as microbial oxidation of organic compounds coupled to electron transfer to the anode.
Figure 3:
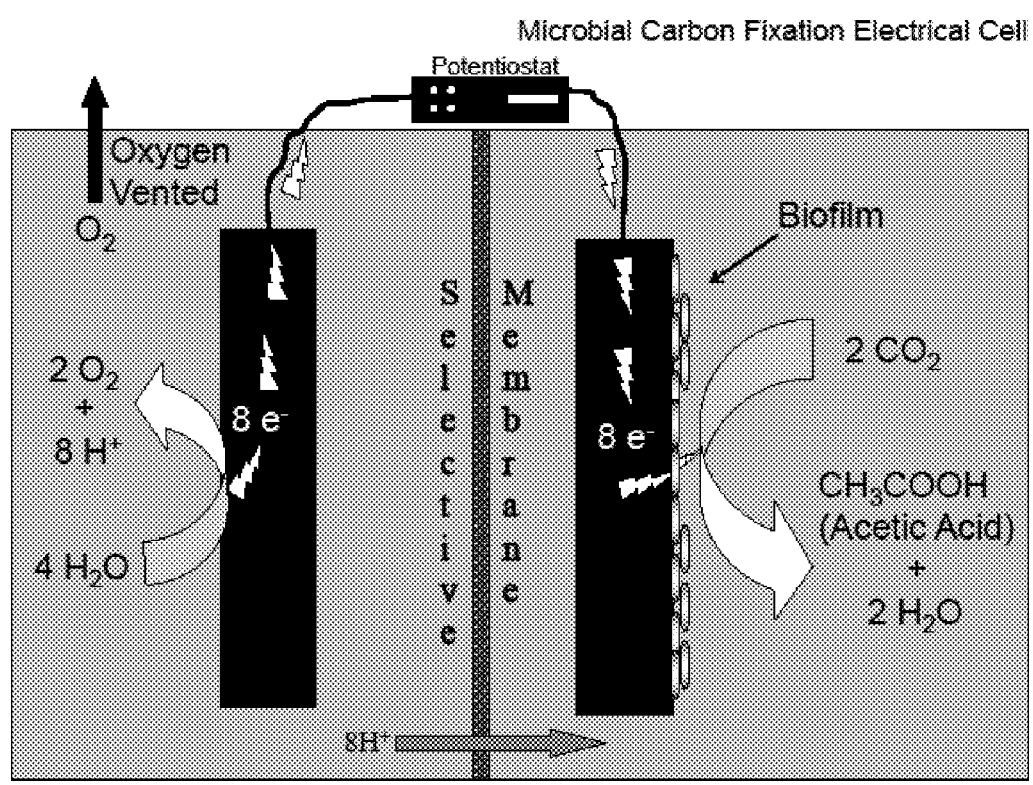
FIG. 3 is an illustrative schematic diagram that shows the configuration of a cell that uses an electrode system to produce carbonaceous compounds having at least two carbon atoms from carbon dioxide as a source of carbon.
Figure 4:
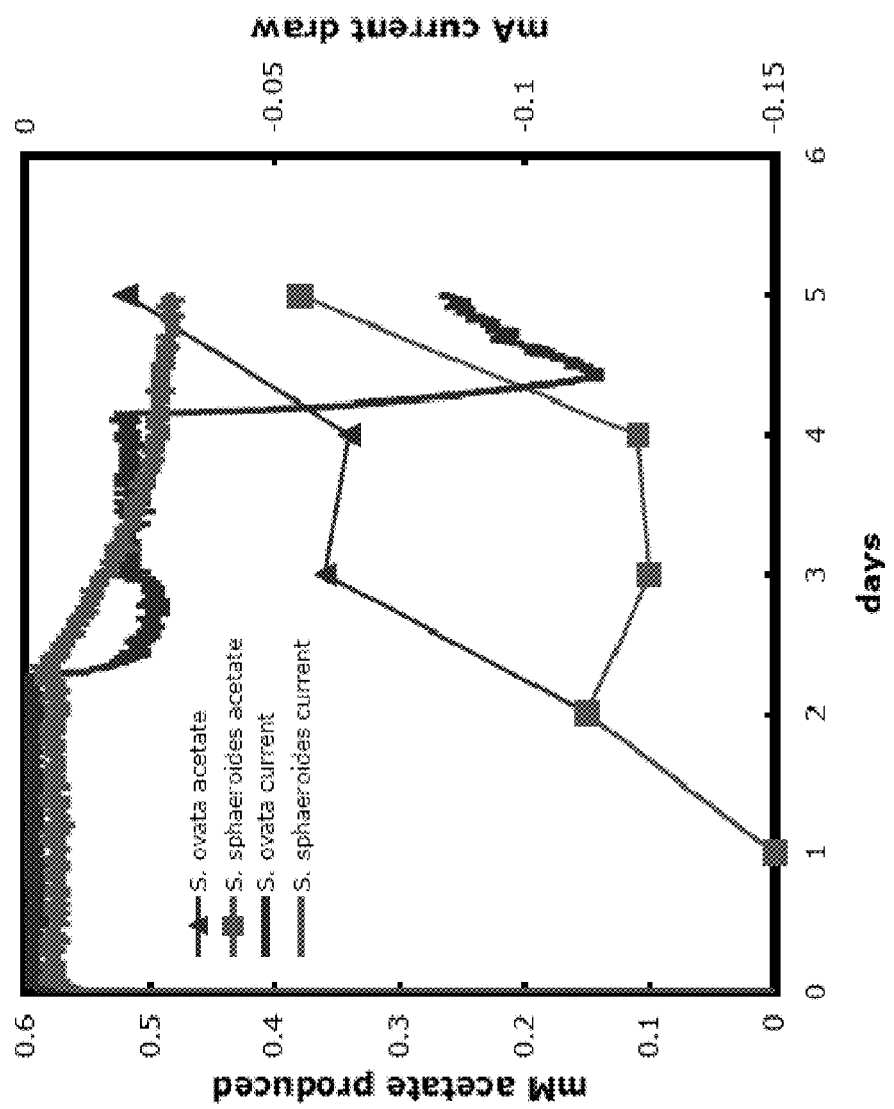
FIG. 4 is a graph that shows the increasing amounts of acetate produced by *Sporomuas* species as more electricity is drawn by the cell of FIG. 3, according to principles of the invention.
Figure 5A:
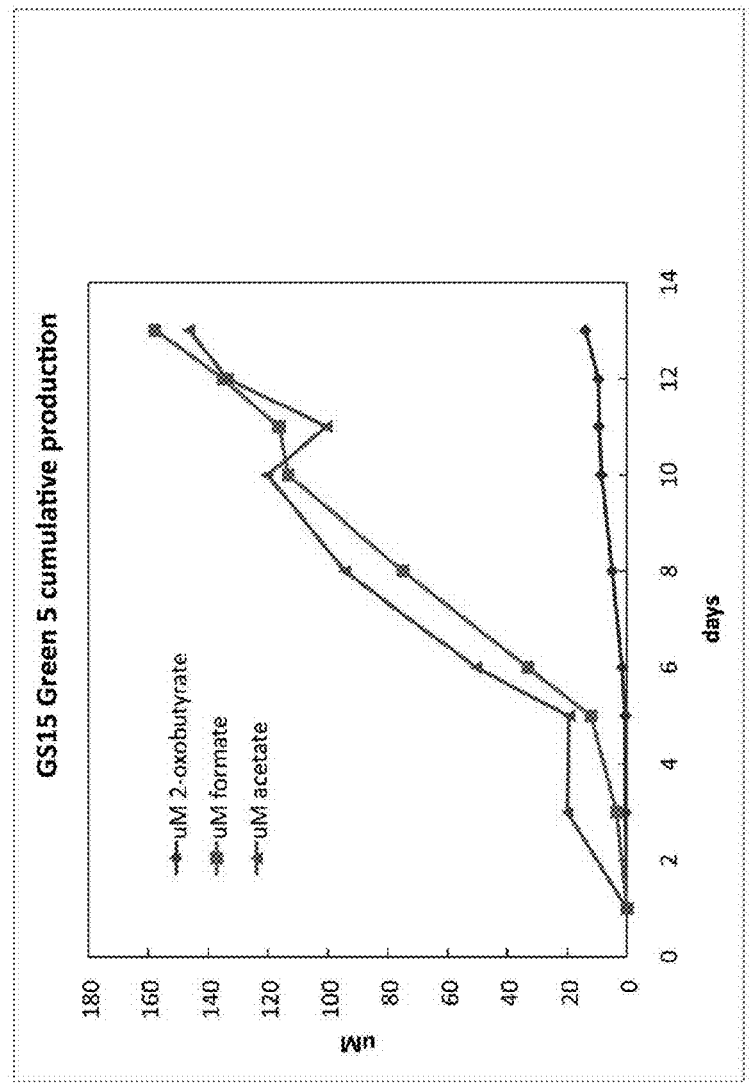
FIG. 5A is a graph that shows the time evolution of amounts of several compounds containing a plurality of carbon atoms that were produced by *Geobacter metallireducens* using carbon dioxide as a source of carbon in systems constructed and operated as described in the present disclosure.
Figure 5B:
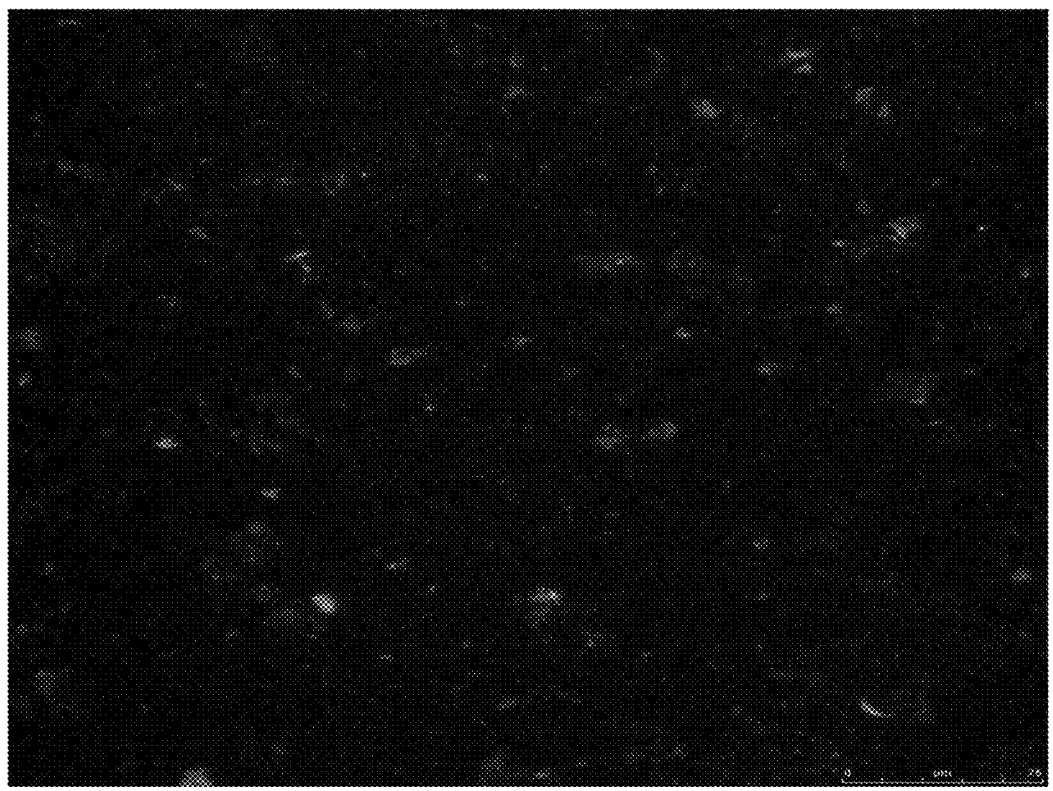
FIG. 5B shows a confocal scanning laser microscopic image of cathode surface with biofilms of *Geobacter metallireducens*. Cells were stained with LIVE/DEAD BacLight viability stain.

FIG. 3 is an illustrative schematic diagram that shows the configuration of a cell that uses an electrode system to produce carbonaceous compounds having at least two carbon atoms from carbon dioxide as a source of carbon. The reaction apparatus of FIG. 3 is a microbial reductive cell similar to those previously demonstrated for the reduction of nitrate, fumarate, U(VI), and chlorinated compounds with *Geobacter* or *Anaeromyxobacter* species shown in FIG. 2. In the embodiments shown, it is comprised of two chambers separated by a membrane. The membrane may be of various compositions including, the proton-selective membrane Nafion. The reaction apparatus of the invention comprises at least two electrodes. One is the cathode which provides the electrons to the microorganisms. Microorganisms attach to the cathode in order to extract the electrons. The other electrode is the anode. In some embodiments, a reference electrode may be provided so that the potential at a selected one of the anode and the cathode can be controlled relative to the reference potential.

A controller that controls the magnitude and direction of the current flow (e.g., the potentiostat of FIG. 3) forces the current in the reaction apparatus of FIG. 3 to flow in the opposite direction to the current flow that is shown in FIG. 1.

The reaction apparatus of FIG. 3 comprises at least two electrodes. One is the cathode at which the biofilm is provided, and which injects electrons into the bacteria component of the biofilm. Another is the anode. In some embodiments, a reference electrode may be provided so that the potential at a selected one of the anode and the cathode can be controlled relative to the reference potential.

Exemplary conductive electrode materials may include, but are not limited to, carbon paper, carbon cloth, carbon felt, carbon wool, carbon foam, graphite, porous graphite, graphite powder, a conductive polymer, platinum, palladium, titanium, gold, silver, nickel, copper, tin, iron, cobalt, tungsten, stainless steel, and combinations of these. In some embodiments, a pre-inoculated electrode comprises at least one of carbon paper, carbon cloth, carbon felt, carbon wool, carbon foam, graphite, porous graphite, graphite powder, a conductive polymer, platinum, palladium, titanium, gold, silver, nickel, copper, tin, iron, cobalt, tungsten, and stainless steel. The electrodes can be any convenient shape or size and need not be the same in shape, size, or composition. The physical orientation of the electrodes can be any convenient mutual orientation relative to each other. One embodiment has the cathode and anode of equal dimensions and oriented with surfaces parallel to each other.

The reaction apparatus of FIG. 3 comprises a source of carbon dioxide that is provided to maintain a desired $pCO_2$ (or carbon dioxide concentration or activity) in an electrolyte that is present in the reaction apparatus. In different embodiments, the concentration of $CO_2$ is maintained by providing a source of $CO_2$ such as a gaseous source, a chemical containing $CO_2$ as a constituent (such as carbonic acid, $H_2CO_3$, dissolved in water), or a carbonate in solution.

The reaction apparatus of FIG. 3 comprises an electrolyte having chemical properties that are compatible with the electrodes, the biofilm, the source of carbon, and the electrical conductivity required to allow current to flow into and out of the electrodes as needed. In some embodiments the electrolyte is water-based.

Electrodes and Electrode Chambers

A dual-chambered fuel cell was constructed with 54 mm outer diameter (OD) glass tubing and a 22 mm OD pinch clamp assembly. The top of each chamber was sealed with a glass dome attached to a ground glass fitting, and the junction was sealed with silicone grease and thick glove box tape. Sampling ports sealed with butyl stoppers, and aluminum crimps were added to the sides and top of each chamber, while electrodes were introduced from the top by feeding a wire through a butyl stopper in the sampling port. The volume of each chamber, with electrode, was a 250 ml of medium with a 150 ml headspace. The chambers were separated with a cation-selective membrane (Nafion 117; Electrosynthesis, Lancaster, N.Y.). Electrodes were 1×3×0.5 inch sticks of unpolished graphite (grade G10; Graphite Engineering and Sales, Greenville, Mich.). New electrodes were soaked in 1 N HCl, which was changed daily until extractable Fe(II) was below detection. After each use, electrodes were washed in 1 N HCl and 1 N NaOH to remove possible metal and biomass contamination. Connections were made with threaded watertight connectors using no. 20 AWG marine-grade wire (Impulse, San Diego, Calif.) screwed into holes drilled directly in the graphite electrodes. Holes were filled with silver epoxy (Epoxy Technology, Billerica, Mass.) and sealed with epoxy (type 730; Epoxy Technology). A reference electrode (BAS, West Lafayette, Ind.) was introduced into the anode-working electrode chamber by embedding it in a butyl rubber stopper and was sterilized by immersing the electrode and stopper in 5 N HCl for 5 min, rinsing in ethanol, and allowing the electrode to fully dry before placing it in a sampling port.

The cathode (working) and anode (counter) chambers were flushed with sterile, anaerobic gas (80:20 $N_2$:$CO_2$), filled with the appropriate buffer medium (described herein below) and connected to a potentiostat. The anode chamber was bubbled continuously with $N_2$:$CO_2$. The medium in the cathode chambers was stirred at 180 r.p.m. with a magnetic stir bar. The chambers were allowed to equilibrate at −500 mV (versus Ag/AgCl) for 24 h before inoculating with cultures or sediment. Control chambers were treated identically, but were not connected to a potentiostat, and no current was able to flow to the working electrode.

Current measurements for studies were collected directly from potentiostat outputs every 15 s with a Power Laboratory 4SP unit (AD Instruments, Inc., 2205 Executive Circle. Colorado Springs, Colo. 80906) connected to a Power Macintosh computer, and data were logged with CHART 4.0 software (AD Instruments, Mountain View, Calif.). Current (mA) was integrated over time and converted to electrons recovered using the conversions 1 C=1 Amp*second, 1 C=6.24 \$10^{18}$ electrons and 1 mol=6.02 \$10^{23}$ electrons (or 96 500 C $mol^{-1}$). Background current (current at the working electrode in the absence of cells, typically 0.03-0.04 mA) was determined for each experiment and subtracted from all values before calculating total electron recovery. During operation, the cathode was poised at −600 mV vs Ag/AgCl under 80% nitrogen/20% $CO_2$ headspace.

Reaction Conditions

The temperature and media used are given in Tables IA and II presented herein before.

In current drawing mode, organic carbon sources, electron acceptors and reductants are omitted.

Media

Media are described below. For media described as DSMZ media, the information provided is available at the web site of the German Collection of Microorganisms and Cell Cultures (Deutsche Sammlung von Mikroorganismen and Zellkulturen GmbH).

| Freshwater media | | |
|---|---|---|
| Component | Quantity | Units |
| $NaHCO_3$ | 2.50 | g |
| $NH_4Cl$ | 1.50 | g |
| $NaH_2PO_4$ | 0.60 | g |
| KCl | 0.10 | g |
| Na-acetate | 2.50 | g |
| Vitamin solution (see DL Vitamin Solution) | 10.00 | ml |
| Trace element solution (see DL Mineral Mix) | 10.00 | ml |
| $Na_2WO_4 \times 2\ H_2O$ | 0.25 | mg |
| Distilled water | 980 | ml |

Preparation and Use:
Adjust pH to 6.7-7.0. medium anaerobically under 80% $N_2$+20% $CO_2$ gas mixture, then add other medium ingredients.

| DL Mineral Mix 1 Liter | |
|---|---|
| Ingredient | 1 L |
| Milli-Q $H_2O$ | 800 ml |
| NTA Trisodium Salt (Free acid) | 1.5 g |
| $MgSO_4$ | 3.0 g |
| $MnSO_4$ * $H_2O$ | 0.5 g |
| NaCl | 1 g |
| $FeSO_4$ * 7 $H_2O$ | 0.1 g |
| $CaCl_2$ * 2 $H_2O$ | 0.1 g |
| $CoCl_2$ * 6 $H_2O$ | 0.1 g |
| $ZnCl_2$ | 0.13 g |
| $CuSO_4$ * 5 $H_2O$ | 0.01 g |
| $AlK(SO_4)_2$ * 12 $H_2O$ | 0.01 g |
| $H_3BO_3$ | 0.01 g |
| $Na_2MoO_4$ * 2 $H_2O$ | 0.025 g |
| $NiCl_2$ * 6 $H_2O$ | 0.024 g |
| $Na_2WO_4$ * 2 $H_2O$ | 0.025 g |
| Complete volume with Milli-Q $H_2O$ to | 1000 ml |

Preparation and Use:
Use iron-free beaker and stir bar
1. Put 800 ml milli-Q water into a beaker with a stir bar
2. Add all ingredients
3. Allow to mix and dissolve completely
4. Complete volume with milli-Q water in a graduated cylinder
5. Store at 4° C.

| DL Vitamin Solution 1 Liter | |
|---|---|
| Ingredient | 1 L |
| Milli-Q $H_2O$ | 800 ml |
| Stored in Refrigerator | |
| Biotin | 0.002 g |
| Pantothenic Acid | 0.005 g |
| B-12 | 0.0001 g |
| p-aminobenzoic acid | 0.005 g |
| Stored in Vitamin Box | |
| Thioctic Acid (alpha lipoic) | 0.005 g |
| Nicotinic Acid | 0.005 g |
| Thiamine | 0.005 g |
| Riboflavin | 0.005 g |
| Pyridoxine HCl | 0.01 g |
| Folic Acid | 0.002 g |
| Complete volume with Milli-Q $H_2O$ to | 1000 ml |

Preparation and Use:
Use iron-free beaker and stir bar
Protect solution from light
1. Put 800 ml milli-Q water into a beaker with a stir bar
2. Add all ingredients
3. Allow to mix and dissolve completely
4. Complete volume with milli-Q water in a graduated cylinder
5. Store at 4° C. in a dark bottle Compositions of and direction for preparing DSMZ Medium 60, DSMZ Medium 135, DSMZ Medium 311, DSMZ Medium 826 and DSMZ Medium 879 are presented in Appendix A.

Additional Biological Systems

It is believed that the acetogens listed hereinbelow are expected to operate to produce compounds that contain more than one carbon atom using carbon dioxide as a source of carbon, using systems and methods as described herein.

In the following list, the Genus is given in bold, and species within that genus are listed in groups,

Acetimaculum *ruminus*
Acetobacterium sp. *bakii, carbinolicum, fimetarium, malicum, paludosum, psammolithicum tundrae, wieringae*
Acetonema *longum*
Acetohalobium *arabatium*
Butyribacterium *methylotrophicum*
Caloramator *fervidus*
Clostridium sp. *autoethanogenum, difficile* AA1, *formicoaceticum, glycolicum* RD-1, *magnummayombei, methoxybenzovorans, scatologenes* SL1, *scatologenes, ultunense*
Eubacterium sp. *aggregans, limosum*
Holophaga *foetida*
Moorella sp. *glycerini, thermoautotrophica*
Natronella *acetigena*
Natronicola *histidinovorans*
Oxobacter *pfennigii*
Ruminococcus *hydrogenotrophicus*
Sporomusa sp. *acidovorans, malonica, paucivorans, termitida*
Syntrophococcus *sucromutans*
Thermoacetogenium *phaeum*
Thermoanaerobacter *kivui*
Treponema sp. *bryantii*, sp. ZAS-1, sp. ZAS-2

To make this a commercially viable technology (e.g., to provide systems and methods that produce larger quantities per unit time, to produce a more pure product, or to produce a specific chemical product), it may be advantageous to genetically tailor *Geobacter* or acetogenic bacteria, or to introduce heterologous genes.

It is expected that solar energy (e.g., photovoltaic solar cells or photoelectrochemical solar cells), solar thermal energy used to run a generator, wind turbines, hydroelectric or biomass-fired electrical generators, or other renewable energy sources of electricity can be used to power the production of organic compounds (e.g. butanol, acetic acid) in microbial reactor cells. In other embodiments, the source of electrical current can be any convenient source of electrical current, including a grid-connected power supply, a battery, a fuel-powered generator (such as a natural gas, propane, kerosene, gasoline or diesel powered generator), or an electrochemical cell power supply. In some embodiments, the electrical current provided can be controlled by a computer-based control system, a manual control system, or a power controller.

It is expected that other systems using the same principles may be useful to provide other carbon-bearing chemicals in a manner similar to the systems and methods described herein.

U.S. patent application, entitled "Systems and Methods for Microbial Reductive Dechlorination of Environmental Contaminants," U.S. Ser. No. 12/538,744, filed on Aug. 10, 2009, which claimed the priority and benefit of U.S. Ser. No. 61/087,450, filed Aug. 8, 2008, is assigned to the common assignee of the present application. The disclosure of each of the above-identified applications is incorporated herein by reference in its entirety.

Background on Non-biological Electrosynthesis of Organic Compounds

Reaction thermodynamics suggests that it should be readily feasible to electrochemically reduce carbon dioxide to a diversity of organic compounds, and this process has been studied for over a hundred years. However, in practice, abiotic electrochemical reduction of carbon dioxide has not proven practical in large part due to (i) poor long-term stability of the cathodes, (ii) nonspecificity of products produced, (iii) sluggishness of carbon dioxide reduction, (iv) competition with hydrogen production, and (v) cathode expense. Incorporating enzyme catalysts on electrodes may promote more specific product formation from electrochemical reduction of carbon dioxide and lower the energy required for reduction, but experiments on enzymatic reduction have typically lasted only a matter of hours, reflecting the fact that enzymes adsorbed to electrodes do not have long-term stability.

Background on Microbe—Electrode Interactions

Various reviews have recounted the last century of the study of microbe-electrode interactions. The ability of microorganisms to transfer electrons to electrodes without the addition of an exogenous electron shuttling mediator was known about a century ago (Potter, M. C. (1911) Electrical effects accompanying the decomposition of organic compounds. *Proc R Soc Lond B* 84: 260-276), despite the often cited report claiming that this phenomenon is a recent discovery.

In contrast to the long history of the study of direct microbial electron transfer to electrodes, the history of direct electron flow in the opposite direction, from electrodes to microorganisms, is rather short with the first report appearing in 2004 (Gregory, K. B., Bond, D. R., and Lovley, D. R. (2004) Graphite electrodes as electron donors for anaerobic respiration. *Environ Microbiol* 6: 596-604). Prior to this there was substantial study on a wide diversity of redox active molecules that can function as electron shuttles, accepting electrons from electrodes and delivering the electrons to microorganisms to influence fermentation patterns or promote the reduction of inorganic electron acceptors. Electron shuttles can typically be reduced at higher electrode potentials than protons, thus saving energy. However, electron shuttles add cost and may lack long-term stability. The toxicity of many shuttles precludes their use in open environments and shuttles must be separated from products and removed from discharge water in reactor applications. Both shuttles and hydrogen promote the proliferation of planktonic cells in contrast with the electrode-attached cells resulting from direct electron transfer. Electrode-attached cells remain separate from products and make it feasible to directly feed specific microorganisms in a defined location in environmental applications.

The first evidence for direct electron transfer from electrodes to microorganisms came from studies with *Geobacter* species. A diversity of *Geobacter* species are now known to reduce a variety of electron acceptors, including nitrate, fumarate, U(VI) and chlorinated solvents as electron acceptors. Data directly demonstrating or suggestive of direct electron transfer from electrodes to additional microorganisms and a wider diversity of electron acceptors is beginning to rapidly accumulate.

Figure 7:
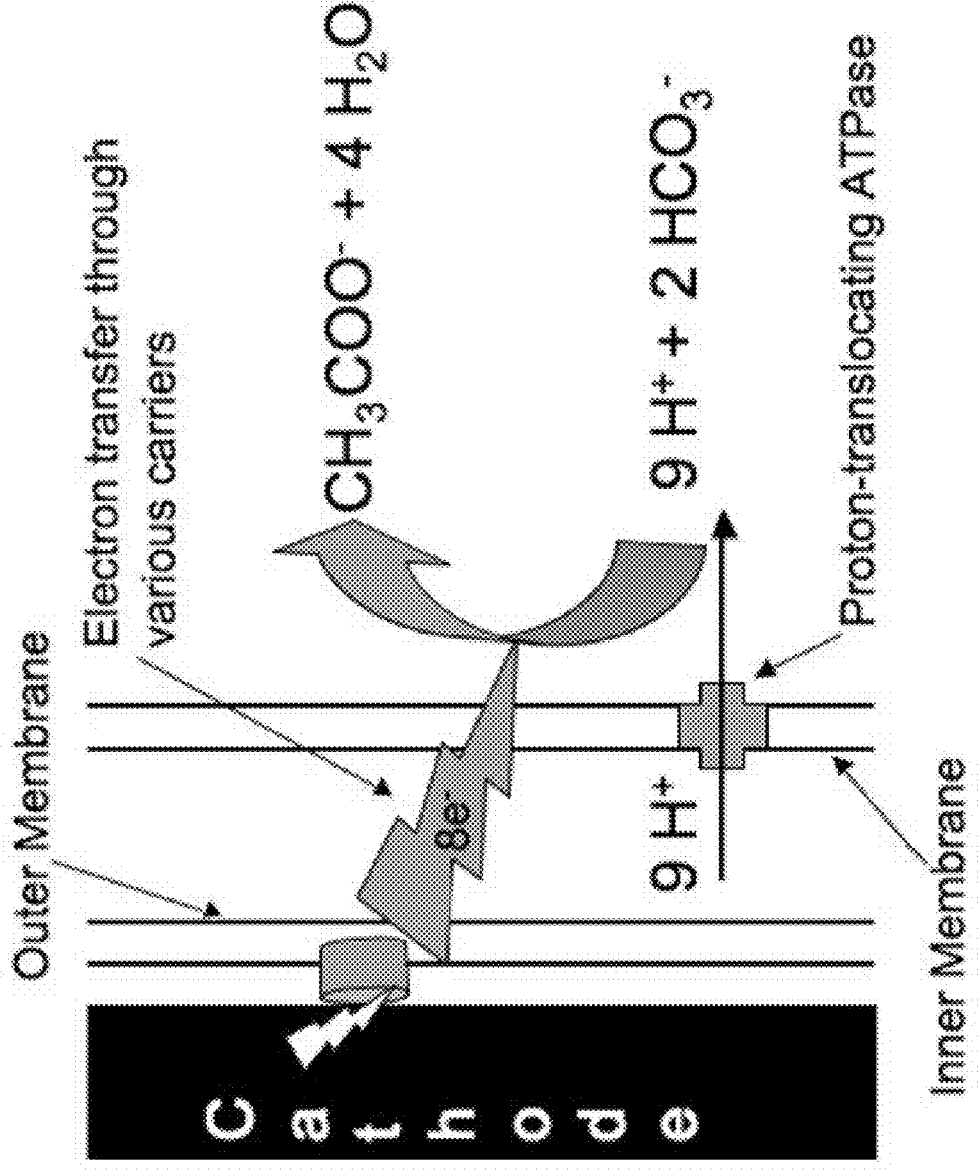
FIG. 7 is a diagram that illustrates a mechanism for energy conservation with an electrode serving as the sole electron donor and carbon dioxide as the sole electron acceptor. The reduction of other electron acceptors on the cytoplasmic side of the inner membrane will also consume protons, leading to a proton gradient across the inner membrane.

Growth with an electrode serving as an electron donor is theoretically possible when common electron acceptors are reduced on the inner side of the inner membrane or in the cytoplasm. See FIG. 7. This is because the reduction of these electron acceptors consumes protons for the production of the reduced end product. Consumption of protons within the cytoplasm will result in a proton gradient across the inner membrane.

The mechanisms for electron exchange between electrodes and *Geobacter* species when electrodes serve as the electron donor are unknown. When *G. sulfurreducens* oxidizes acetate with electron transfer to electrodes it forms thick (>50 mm) biofilms and even cells at this substantial distance from the anode are considered to contribute to current production. The working model for electron transfer to the anode in thick *G. sulfurreducens* biofilms is that conductive pili are responsible for electron transfer through the bulk of the biofilm, but outersurface c-type cytochromes are required to facilitate electron transfer between the biofilm and the anode surface.

However, current-consuming fumarate-reducing biofilms of *Geobacter* species are much thinner than current-producing biofilms. Gene expression patterns in current-consuming cells are very different than those in current-producing cells and deletion of genes that are essential for current production do not impact on current consumption and vice versa. These results suggest that the routes for electron transfer from electrodes to cells may be different than they are for current production.

Production of Fuels and Chemicals

Microbial electrosynthesis offers the possibility of greatly increasing the value of electrical energy that can be harvested with renewable energy strategies such as solar and wind because it is feasible to a produce a wide range of valuable chemical products that would otherwise need to be synthesized from petroleum or biomass. The production of liquid transportation fuels with microbial electrosynthesis is particularly attractive. This is because electricity generation with renewable technologies is not continuous or always synched with demand and it is difficult to store electricity. Large-scale fuel production could readily convert electrical energy into covalent carbon bonds permitting storage and delivery upon demand within existing infrastructure.

Microbial reduction of carbon dioxide with the release of extracellular, multi-carbon products is the most preferable form of microbial electrosynthesis because most desired products will have more than one carbon, and extracellular release of products from cells attached to electrodes simplifies product recovery. This form of microbial electrosynthesis is feasible with some acetogenic bacteria. For example, the acetogen *Sporomusa ovata* formed biofilms on graphite electrodes and could accept electrons directly from the electrodes with the reduction of carbon dioxide to acetate and small amounts of 2-oxobutyrate. Over 85% of the electrons consumed in the system were recovered in these products.

These results suggest that the reduction of carbon dioxide with electrons derived directly from electrodes can be an effective process for converting carbon dioxide to extracellular, multi-carbon products. The fact that acetyl-CoA is an intermediate in acetate production in acetogens suggests that it may be possible to engineer the production of a wide diversity of products. For example, butanol is a desirable transportation fuel and it has already been demonstrated that it is possible to express genes for butanol production in the acetogen *Clostridium ljungdahlii*. *Clostridium ljungdahlii* can use an electrons derived from an electrode to reduce carbon dioxide to acetate and other products (FIG. 13), including butanol.

Figure 8:
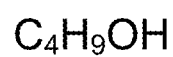
FIG. 8 is a diagram that shows the four isomeric alcohols of formula $C_4H_9OH$, any or all of which can be referred to generally as butanol.
Figure 8:
Figure 8:
Figure 8:
Figure 8:
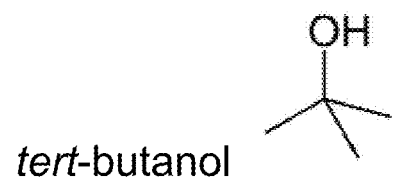

Butanol or butyl alcohol can refer to any of the four isomeric alcohols of formula $C_4H_9OH$, including n-Butanol, butan-1-ol, 1-butanol, n-butyl alcohol; Isobutanol, 2-methylpropan-1-ol, isobutyl alcohol; sec-Butanol, butan-2-ol, 2-butanol, sec-butyl alcohol; and tert-Butanol, 2-methylpropan-2-ol, tert-butyl alcohol. It can also refer to butanol fuel, which is a proposed alternative to gasoline. See FIG. 8 for the chemical diagrams illustrating the four isomers.

Figure 9A:
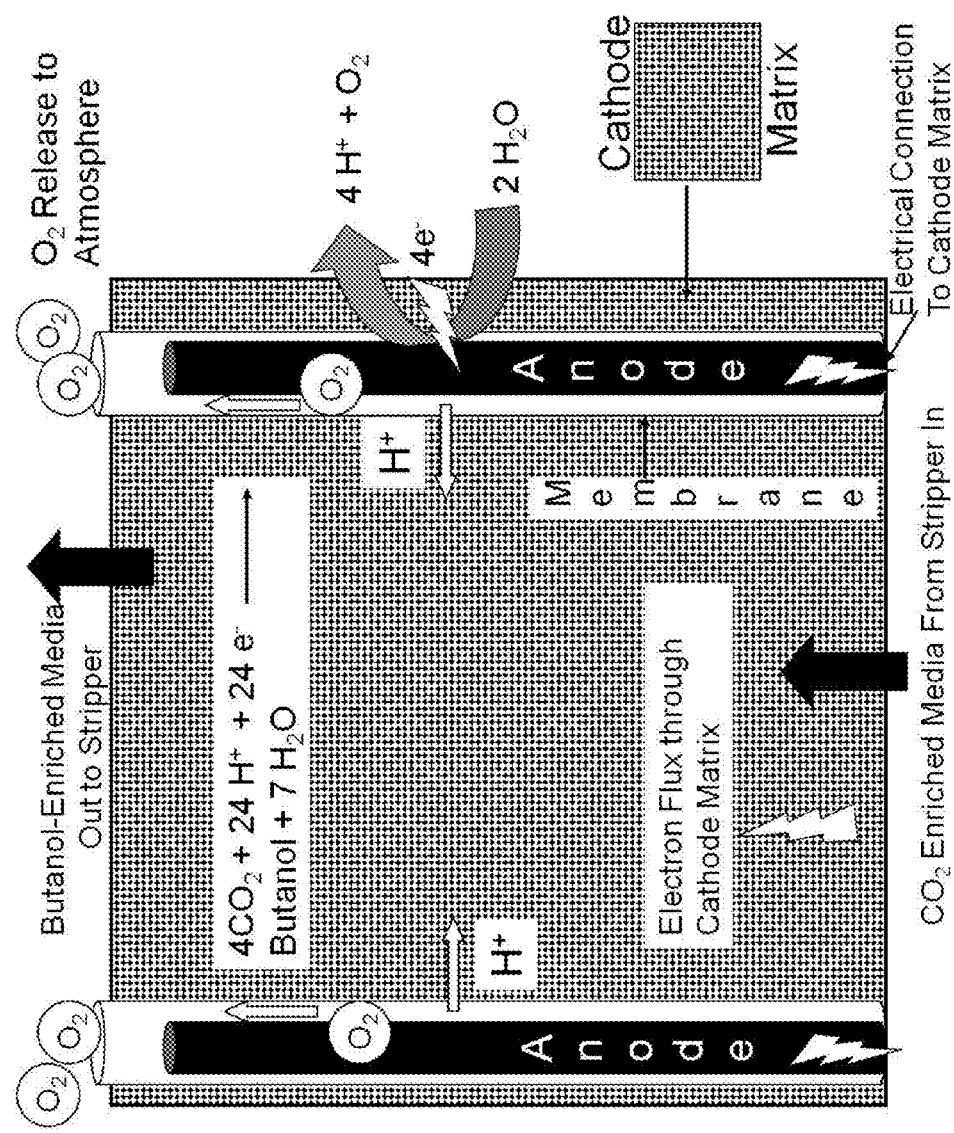
FIG. 9A is a diagram that illustrates a chemical reaction according to principles of the invention that occurs in a reaction chamber with a high surface area cathode matrix.

FIG. 9A is a diagram illustrating a reaction chamber in which the cathode and anode are in the same vessel. As illustrated in FIG. 9A, an electrically driven reaction that consumes water and $CO_2$ is conducted with the generation of butanol at the cathode and molecular oxygen at the anode.

As illustrated in FIG. 9A, the electrically driven reaction at the cathode using $CO_2$ to generate butanol and water is:

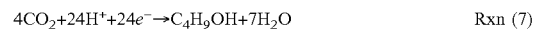

$$4CO_2 + 24H^+ + 24e^- \rightarrow C_4H_9OH + 7H_2O \quad \text{Rxn (7)}$$

Combining Rxn (7) with 6 times Rxn (3), we get the net reaction consuming $CO_2$ and water to generate butanol and oxygen:

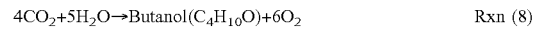

$$4CO_2 + 5H_2O \rightarrow Butanol(C_4H_{10}O) + 6O_2 \quad \text{Rxn (8)}$$

We can write an equation for a generic reaction to produce a hydrocarbon and molecular oxygen from carbon dioxide and water as:

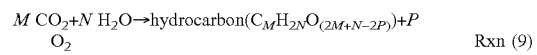

$$M\,CO_2 + N\,H_2O \rightarrow \text{hydrocarbon}(C_M H_{2N} O_{(2M+N-2P)}) + P\,O_2 \quad \text{Rxn (9)}$$

We can also write this generic equation as:

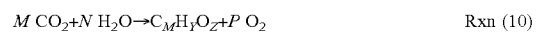

$$M\,CO_2 + N\,H_2O \rightarrow C_M H_Y O_Z + P\,O_2 \quad \text{Rxn (10)}$$

where M, N and P are non-negative numbers and Y=2N, and Z=2M+N−2P. For butanol, M=4, N=5, P=6, 2N=10, 2M+N−2P=8+5−12=1.

Other compounds that have been produced include propanol, ethanol, 2-oxobutyrate, and formate. We have developed strategies for growing microorganisms to change the products they produce. For example, if we grow *Geobacter metallireducens* on butanol first, then it will make butanol when grown on the cathode. We have genetically engineered a strain of *Geobacter metallireducens* so that it can make propanol. We have used a genetically engineered strain of *Clostridium ljungdahlii* to produce butanol. Many other products are readily imagined.

Figure 9B:
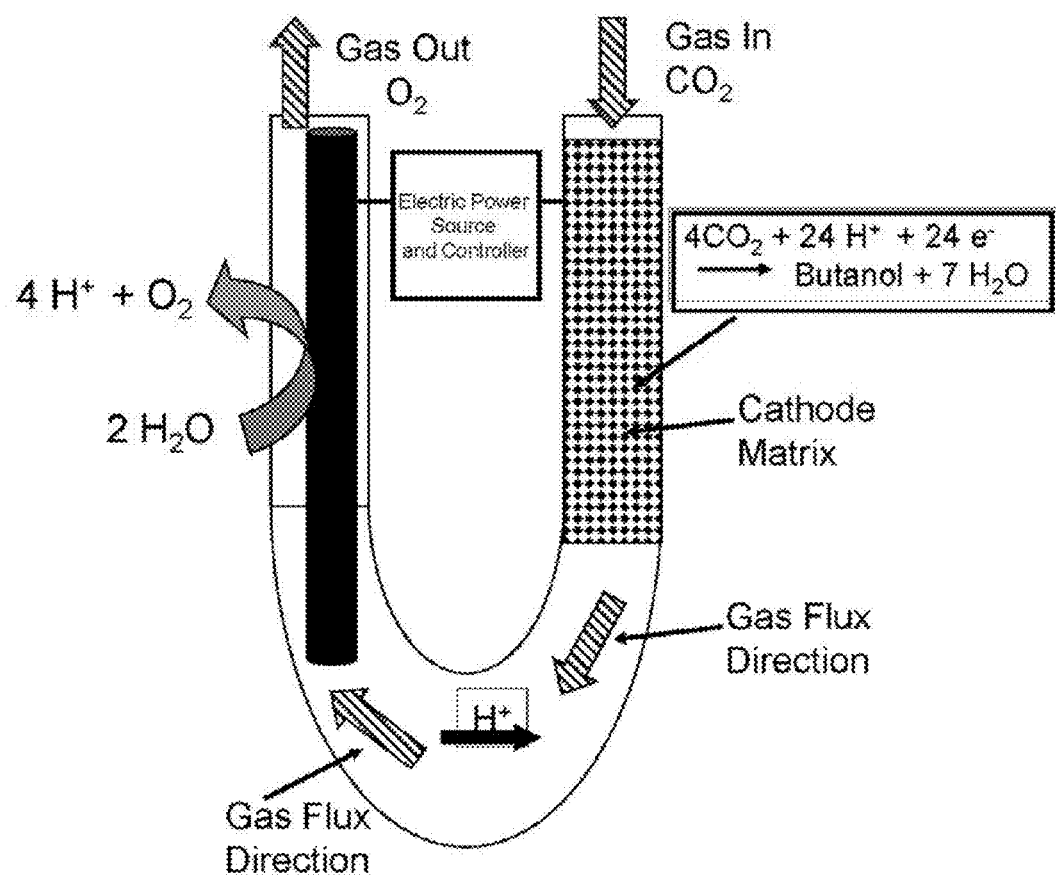
FIG. 9B is a diagram that illustrates a chemical reaction according to principles of the invention that occurs in a reaction chamber that does not require a semi-permeable membrane to separate the anode and the cathode.

Other reaction designs to carry out these reactions are possible. For example, FIG. 9B illustrates a strategy in which membrane is not required in order to separate the anode and the cathode reactions.

Continuous Operation

Figure 17:
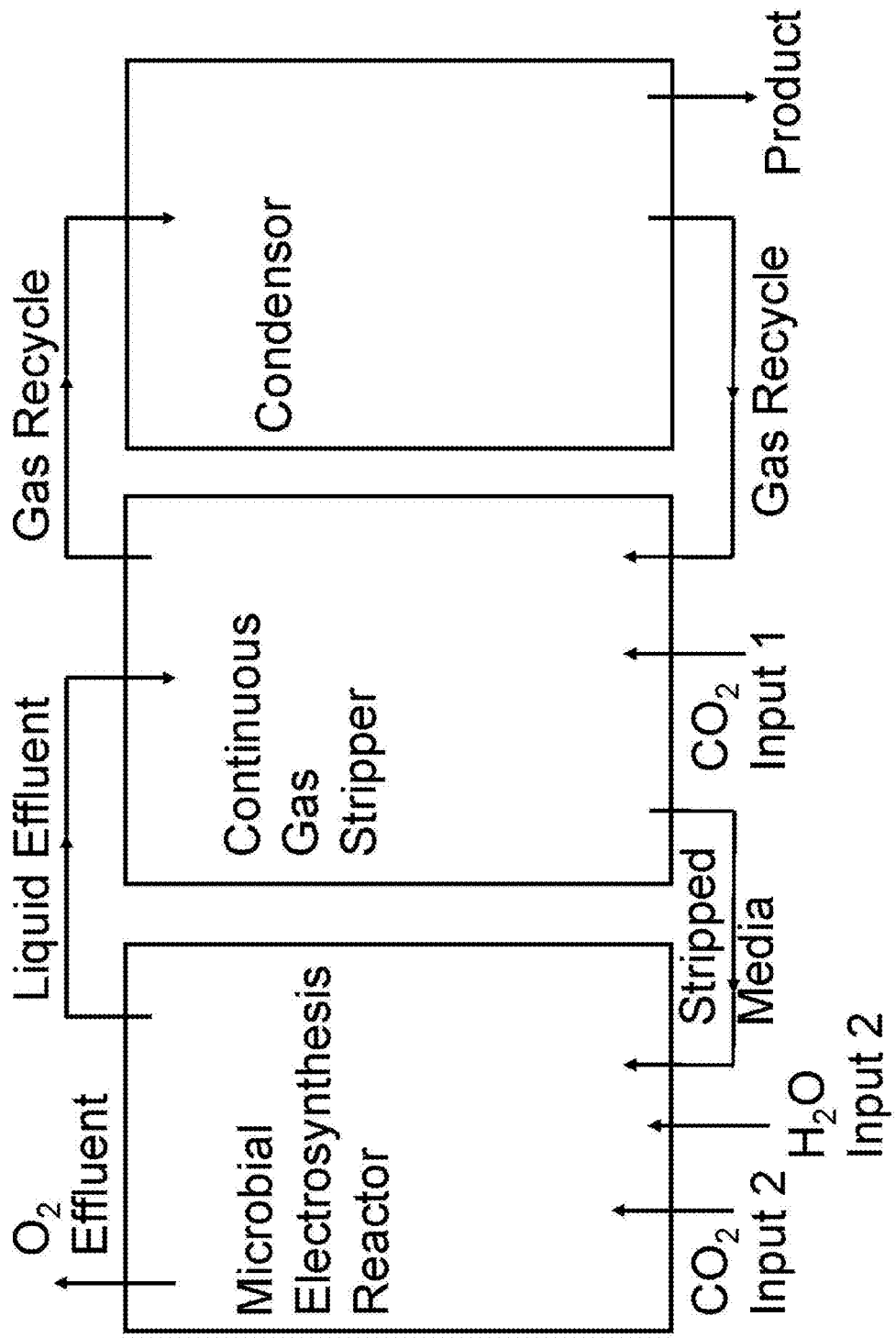
FIG. 17 shows a schematic flow diagram for continuous flow operation for a reaction that consumes CO2 and water and produces a hydrocarbon and molecular oxygen according to principles of the invention.

Large-scale microbial electrosynthesis is expected to perform most optimally as a continuous flow system. FIG. 17 shows a schematic flow diagram for continuous flow operation for a reaction that consumes $CO_2$ and water and produces a hydrocarbon and molecular oxygen according to principles of the invention. An example using butanol as a hydrocarbon will be provided. Butanol is produced in the microbial electrosynthesis reactor, with water and carbon dioxide provided as reagents, and $O_2$ produced as a product. In some embodiments, $CO_2$ is introduced into the microbial electrosynthesis reactor as a feedstock. In some embodiments, makeup water is introduced into the microbial electrosynthesis reactor as a feedstock. Butanol-enriched water resulting from the reaction of carbon dioxide and water to butanol in the microbial electrosynthesis reactor exits the microbial electrosynthesis reactor and is fed into a continuous gas stripper, which strips butanol from solution. The stripped butanol is collected in a condenser. Gas stripping and condensation is a well-established conservative technology that is considered to be the most effective method for purifying butanol. Carbon dioxide-rich gas can be introduced into the stripper to serve as the stripping agent. Additional $CO_2$ gas can be added as needed to compensate for carbon dioxide utilization. The medium that has been stripped of butanol is recycled into the microbial electrosynthesis reactor. Other hydrocarbons can be produced in similar fashion, using a suitable separation technology to remove and recover the hydrocarbon from the aqueous reaction medium.

Reducing carbon dioxide to multicarbon organic chemicals and fuels with electricity is an attractive strategy to convert solar energy that is harvested intermittently with photovoltaic technology and store the energy in covalent chemical bonds. The organic compounds produced can then be distributed via existing infrastructure. Current-driven microbial carbon dioxide reduction represents a new form of photosynthesis that is expected to convert solar energy to organic products more effectively than traditional biomass-based strategies.

Culturing in H Cells

We evaluated the possibility of feeding an acetogen electrons from an electrode with *Sporomusa ovata* (Deutsche Sammlung Mikroorganismen and Zellkulturen [DSMZ] culture 2662). Cells were grown in the cathode chambers of "H cells" (see FIG. 6A), which have previously been used to evaluate other forms of electrode-driven anaerobic respiration. The cathode and anode were comprised of unpolished graphite sticks. The anode and cathode chambers, each containing 200 ml of medium, were separated with a Nafion cation-exchange membrane. A potentiostat maintained a potential difference between the anode and cathode. Electrons extracted from water at the anode were delivered to the cathode at −400 mV (versus standard hydrogen electrode), a potential well above the −600 mV necessary to produce even low levels of hydrogen with unpolished graphite. The lack of hydrogen production was verified by directly measuring hydrogen concentrations with a reduction gas analyzer. In most instances, the electrical current was obtained from a standard electrical outlet, but a solar-powered potentiostat (FIG. 6A), comprised of a solar panel and voltage control unit built with standard electrical components, could also support the system.

An inoculum of *S. ovata* was grown with hydrogen as the electron donor ($H_2$—$CO_2$ [80:20]) in the DSMZ-recommended growth medium (DSMZ 311) with betaine, Casitone, and resazurin omitted. The hydrogen-grown cells were introduced into the cathode chamber in the same medium but with the yeast extract and the cysteine and sulfide reductants omitted. This bicarbonate-based medium contained no organic compounds other than a vitamin mixture, and carbon dioxide was the sole electron acceptor. The culture was initially bubbled with a hydrogen-containing gas mixture ($N_2$—$OO_2$—$H_2$ [80:13:7]) as an additional electron donor to accelerate the growth of a biofilm on the cathode surface. Acetate was measured with high performance liquid chromatography (HPLC). Once acetate reached 10 mM, 50% of the medium was replaced with fresh medium. This process was repeated three times. This periodic removal of planktonic cells promoted biofilm growth on the cathode. The gas phase was then switched to $N_2$—$CO_2$ (80:20). Once the consumption of current was observed (within 24 h), the system was switched to flow through mode in which fresh medium maintained under $N_2$—$CO_2$ was continuously introduced (0.1 ml/min; dilution rate of 0.03 $h^{-1}$). Hydrogen partial pressures in the headspace remained less than 10 ppm throughout the study, ca. 2 orders of magnitude below the minimum threshold for acetate production from hydrogen by acetogens.

Figures 6A, 6B:
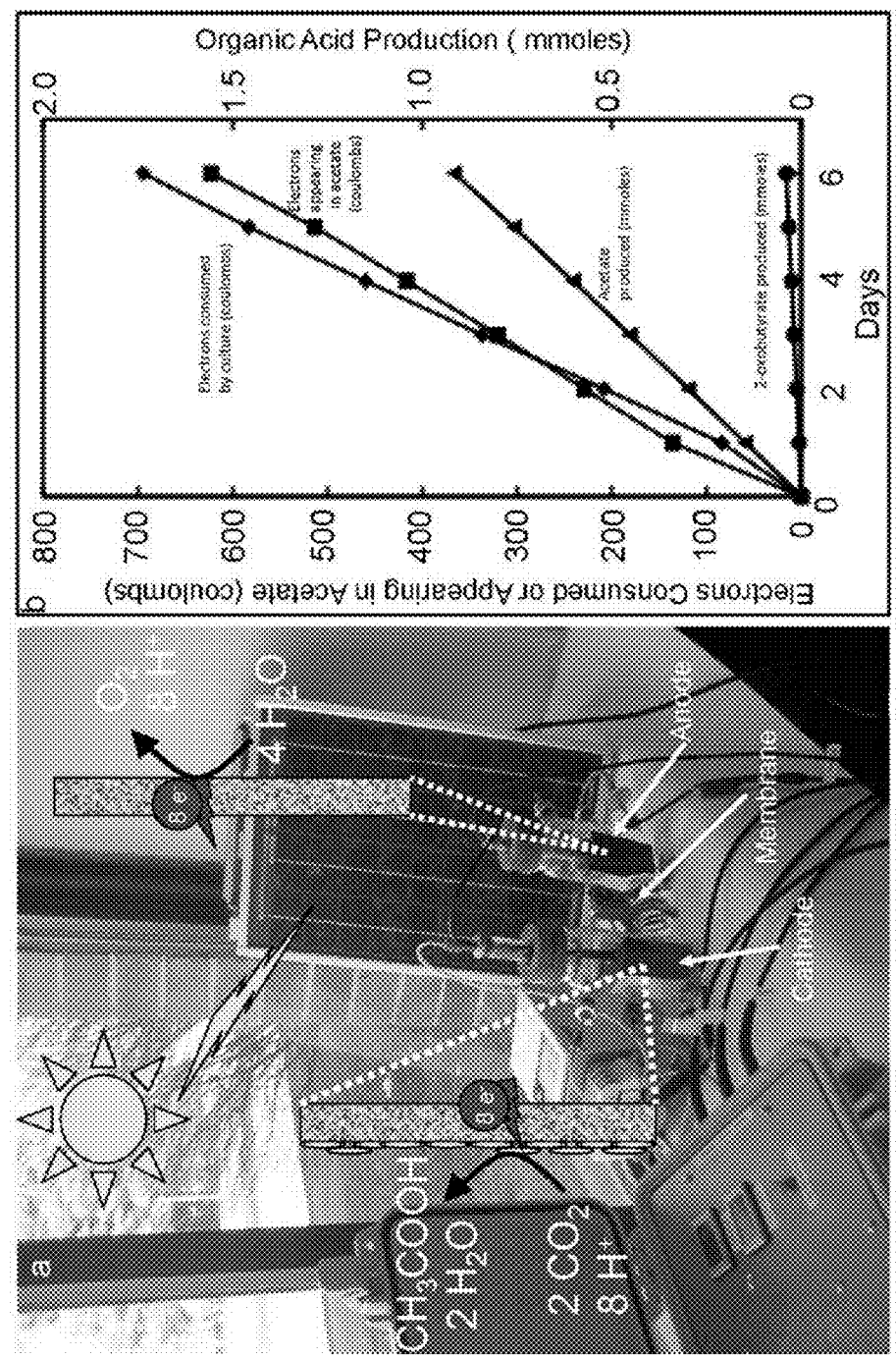
FIG. 6A shows a device (H-cell) for supplying cathode biofilms of *Sporomusa ovata* electrons derived from water. An embodiment that is solar-powered using photovoltaic cells is illustrated.
FIG. 6B is a graph that shows the electron consumption and product formation by a representative *Sporomusa ovata* biofilm over time. The data shown were obtained with a system connected to a standard electric current source. The mean standard errors of the organic acid and current measurements were 2% and 13%, respectively.

Systems with *S. ovata* steadily consumed current with the production of acetate and small amounts of 2-oxobutyrate (FIG. 6B). Uninoculated controls did not consume current or produce organic acids. If the current supply to the *S. ovata* biofilm was interrupted, acetate and 2-oxobutyrate production stopped. Although it was not possible to measure carbon dioxide consumption due to the high concentrations of bicarbonate in the medium, it was possible to calculate an electron balance. Electrons appearing in acetate accounted for a high proportion of the electrons that the cultures consumed (FIG. 6B). In three replicate cultures, the electron recovery in acetate and 2-oxobutyrate was 86%±21% of the electrons transferred at the cathodes. These results demonstrated that *S. ovata* could accept electrons from graphite electrodes with the reduction of carbon dioxide and that most of the electrons transferred from the electrodes to the cells were diverted toward extracellular products, rather than biomass formation. The *S. ovata* cathode biofilms were robust and have been run for periods of more than 3 months without losing their capacity for current consumption and acetate production.

Figures 10A, 10B:
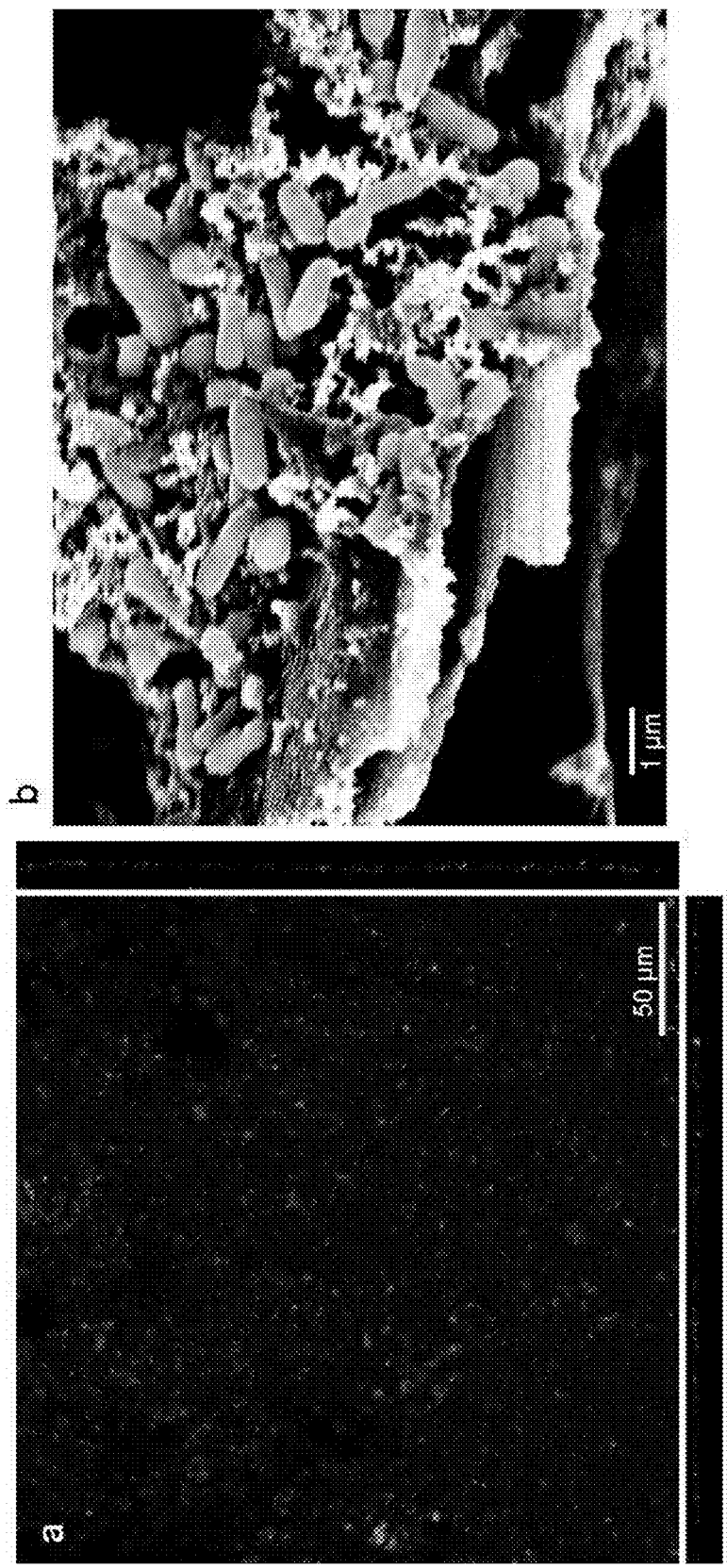
FIG. 10A shows confocal scanning laser microscopic images (top down and side views) of cathode surface with biofilms of *Sporomusa ovata*. Cells were stained with LIVE/DEAD BacLight viability stain.
FIG. 10B shows scanning electron microscopic image of cathode surface with biofilms of *Sporomusa ovata* cells highlighted.

The long-term viability of *S. ovata* biofilms was further evident from confocal scanning laser microscopy of a biofilm that had been fixing carbon dioxide for 3 months. The cells in biofilms treated with LIVE/DEAD BacLight viability stain, stained green, suggesting that they were healthy and metabolically active (FIG. 10A). The biofilms were relatively thin, similar to the biofilms previously described for other microorganisms growing on cathodes. This was further confirmed with scanning electron micrographs of the cathode surface (FIG. 10B), prepared as previously described in the literature. The cells appeared to be intimately associated with the graphite surface, as would be expected for direct electrode-to-cell electron transfer. There was no visible turbidity in the cathode chamber, consistent with previous studies on direct electrode-driven respiration, and further suggesting that biofilm cells were primarily responsible for current consumption and carbon dioxide reduction.

Although acetate has economic value, a more important consideration is that acetate is formed from acetyl coenzyme A (acetyl-CoA), which is the central intermediate for the genetically engineered production of a wide range of chemical commodities as well as potential liquid transportation fuels. The fact that small amounts of 2-oxobutyrate were produced, in addition to acetate, demonstrates that even without any engineering, some carbon and electron flow was diverted away from acetate production. The acetogen *Clostridium ljungdahlii* has recently been genetically engineered to produce the gasoline substitute butanol from acetyl-CoA.

Several other acetogenic bacteria, including two other *Sporomusa* species, *Clostridium ljungdahlii*, *Clostridium aceticum*, and *Moorella thermoacetica* produced consumed current with the production of organic acids. In general acetate was the primary product, but 2-oxobutyrate and formate were also formed with 2-oxobutyrate being the predominant identified product of electrosynthesis by *C. aceticum*. *S. sphaeroides, C. ljungdahlii*, and *M. thermoacetica* had the high (>85%) efficiencies of electrons consumed recovered in identified products. The acetogen *Acetobacterium woodii* was unable to consume current. Enrichments from numerous sources known to contain acetogenic microorganisms produced acetate.

Materials and Methods

Source of Organisms and Culture Maintenance

*Sporomusa ovata* (DSM 2662), *Sporomusa silvacetica* (DSM 10669), *Sporomusa sphaeroides* (DSM 2875), *Clostridium ljungdahlii* (DSM 13528), *Clostridium aceticum* (DSM 1496), *Moorella thermoacetica* (DSM 21394), and *Acetobacterium woodii* (DSM 1030), were obtained from the Deutsche Sammlung Mikroorganismen and Zellkulturen *Geobacter metallireducens* was obtained from our laboratory culture collection.

The cultures were routinely grown with $H_2/CO_2$ (80:20) at 30° C., unless otherwise noted. *Sporomusa* strains were cultured in DSM media 311 omitting betaine, fructose, casitone and resazurin. *C. ljungdahlii* was cultured in DSM media 879 at 37° C. *A. woodii* and *C. aceticum* were cultured in DSM media 135 with resazurin and fructose omitted. *M. thermoacetica* was cultured at 37° C. in DSM media 60 omitting the fructose, glucose and reducing the yeast extract to 1 g/L.

Cathode Biofilms

Each culture was grown on at least four cathodes in 'H-cell' culturing systems as previously described. In these systems graphite stick cathode and anodes are suspended in two chambers, containing 200 ml of medium, which are separated with a Nafion cation-exchange membrane. A potentiostat provides the energy to extract electrons from water at the anode and poise the cathode at −400 mV (versus standard hydrogen electrode). This provides electrons at a sufficiently low potential for microbial electrosynthesis without significant production of $H_2$. Cultures were inoculated into the cathode chamber, containing the medium appropriate for the organism described above, and the culture was bubbled with a hydrogen-containing gas mixture ($N_2/CO_2/H_2$, 80:13:7) as an additional electron donor to promote the growth of a biofilm on the cathode surface. As previously described, the medium was replaced several times to remove planktonic cells and then the gas phase was switched to $N_2/CO_2$ (80:20). For those cultures capable of current consumption, current consumption was observed within 24 hours and at this point fresh medium maintained under $N_2/CO_2$ was continuously introduced (0.1 ml/min; dilution rate 0.03 $h^{-1}$) as previously described.

Enrichment Cultures

Numerous inocula were used to start enrichments directly into electrosynthesis H-cells. Rhizosphere nodules from soybean and green bean plants (Brookfield Farm, Amherst, Mass.) and clover (Chesterfield, Mass.), waterlogged acidic forest soil (Atkins Reservoir, Amherst, Mass.), American toad (*Bufo americanus*) feces were enriched in freshwater medium at 25° C. Eelgrass roots (Nantucket sound, Nantucket, Mass.) and 2 locations from the UMASS Nantucket Field Station salt marsh, one grassy and one center channel (Nantucket, Mass.) were enriched in freshwater medium with 10% salt stock ((grams per liter): NaCl, 18; $MgCl_2 \cdot 6H_2O$, 5.4; $CaCl_2 \cdot 2H_2O$, 0.27) and in artificial seawater (Instant Ocean, United Pet Group, Inc. Cincinnati, Ohio) at 25° C. Crushed termites (*Neotermes jouteli, Cryptotermes califrons, Reticulitermes* sp., *Kalotermes* sp.) where enriched first in freshwater media with $H_2$: $CO_2$ due to small inoculum size and bottles that produced acetate well where then used as a 50% inoculum into electrosynthesis H-cells. Additionally, Nantucket enrichments with $H_2$: $CO_2$ in media were used as a 50% inoculum into electrosynthesis H-cells.

Analytical Methods

Acetate and other organic acids were measured via HPLC. Biofilms were visualized by confocal scanning laser microscopy using LIVE/DEAD BacLight viability stain. Samples of graphite electrode were prepared for SEM using hexamethyldisilazane after ethanol dehydration in order to remove all remaining liquids from the sample. Scanning electron microscopy analysis was performed using a FEG SEM, model JEOL JSM 6320F. Protein was measured with the bicinchoninic acid method (Sigma, St. Louis, Mo.).

Pure Culture Studies

The previous finding that *Sporomusa ovata* was capable of electrosynthesis led to the evaluation of two additional species of *Sporomusa, S. sphaeroides* and *S. silvacetica*. Both *Sporomusa* species consumed current (FIG. 11A and FIG. 11B) and formed thin biofilms on the cathode surface (FIG. 12A and FIG. 12B), similar to those previously reported for *S. ovata* reducing carbon dioxide as the sole electron donor. Cells stained green with Live/Dead stain, suggesting that they were metabolically active, even after extended incubation (FIG. 12A). The greater amount of protein in the *S. silvacetica* biofilms (0.048±0.003 mg/cm²) compared with the *S. sphaeroides* biofilms (0.020±0.0005 mg/cm²) was consistent with the apparent relative biomass abundance in confocal images (FIG. 12A and FIG. 12B) and rates of current consumption (FIG. 11A and FIG. 11B).

Figures 11A, 11B:
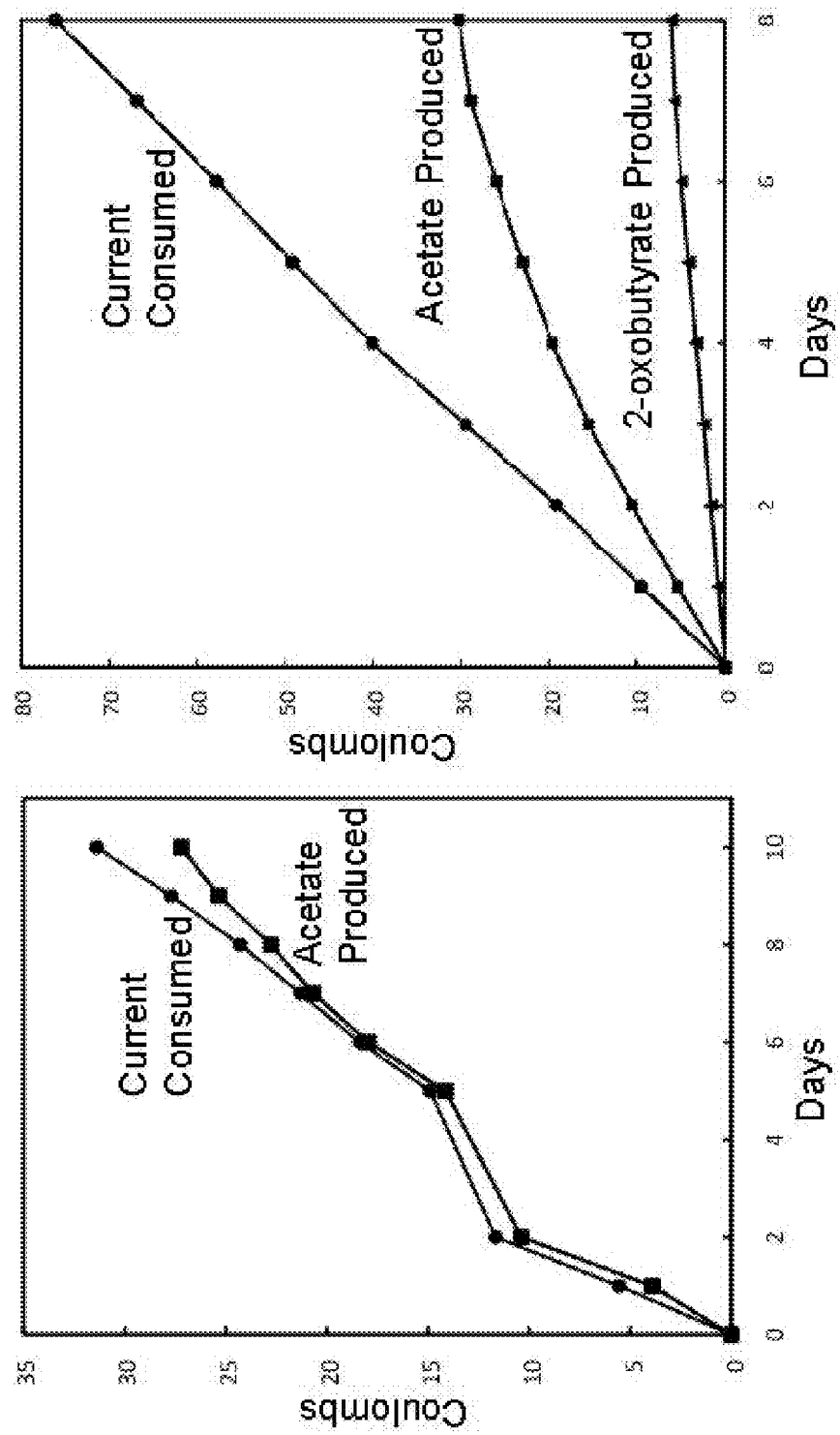
FIG. 11A is a graph showing electron consumption and product formation over time with *Sporomusa sphaeroides*. Results shown are from a representative example of three replicate cultures.
FIG. 11B is a graph showing electron consumption and product formation over time with *Sporomusa silvacetica*. Results shown are from a representative example of three replicate cultures.
Figure 12B:
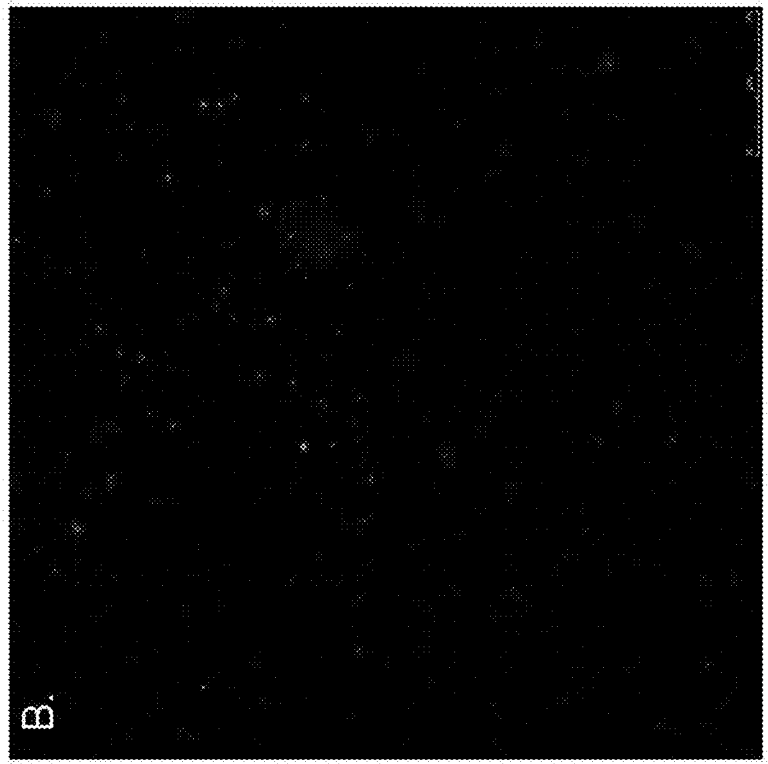
FIG. 12B shows confocal scanning laser microcope images (top down and side views) of *Sporomusa silvacetica* after 3 months of growth on the cathode surface. Cells were stained with LIVE/DEAD BacLight viability stain.
Figure 12A:
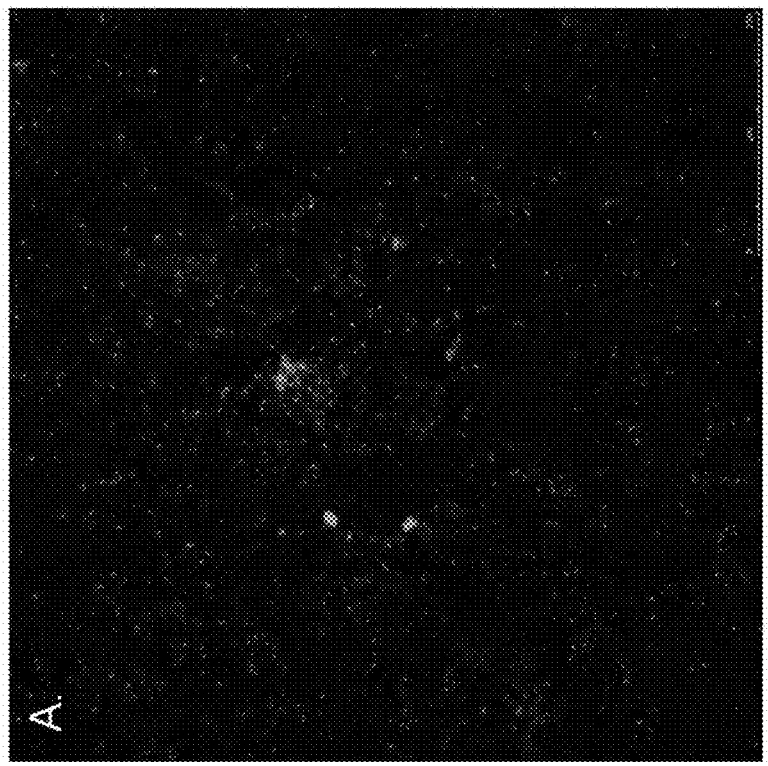
FIG. 12A shows confocal scanning laser microcope images (top down and side views) of *Sporomusa sphaeroides* after 3 months of growth on the cathode surface. Cells were stained with LIVE/DEAD BacLight viability stain.

*Sporomusa sphaeroides* consumed current with the production of acetate (FIG. 11A). Of the electrons consumed as current, 84%±26% (mean±standard deviation) were recovered in acetate. The rate at which *S. sphaeroides* consumed current was 20-fold slower than that previously reported for *S. ovata*. *Sporomusa silvacetica* produced primarily acetate with trace accumulations of 2-oxobutyrate (FIG. 11B). The recovery of electrons in acetate and 2-oxybutrate was only 48±6%, which is attributed to the production of other products, which have yet to be identified as peaks were observed in HPLC analysis that could not be attributed to any of a wide range of potential products/metabolites. Rates of current consumption were better than those of *S. sphaeroides*, but still only about 10% those of *S. ovata*. These results demonstrate that the capacity for electrosynthesis can vary significantly within a single genus.

Although *Sporomusa* species are within the *Clostridium* phylum, they are gram negative as are the *Geobacter* and *Anaeromyxobacter* species that have previously been shown to accept electrons from electrodes. However, a diversity of gram-positive microorganisms have the capacity to produce current in microbial fuel cells, demonstrating that it is possible for gram-positives to establish electrical connections with electrodes. Therefore, the possibility that gram-positive acetogens could reduce carbon dioxide with an electrode as the sole electron donor was evaluated.

Figure 13:
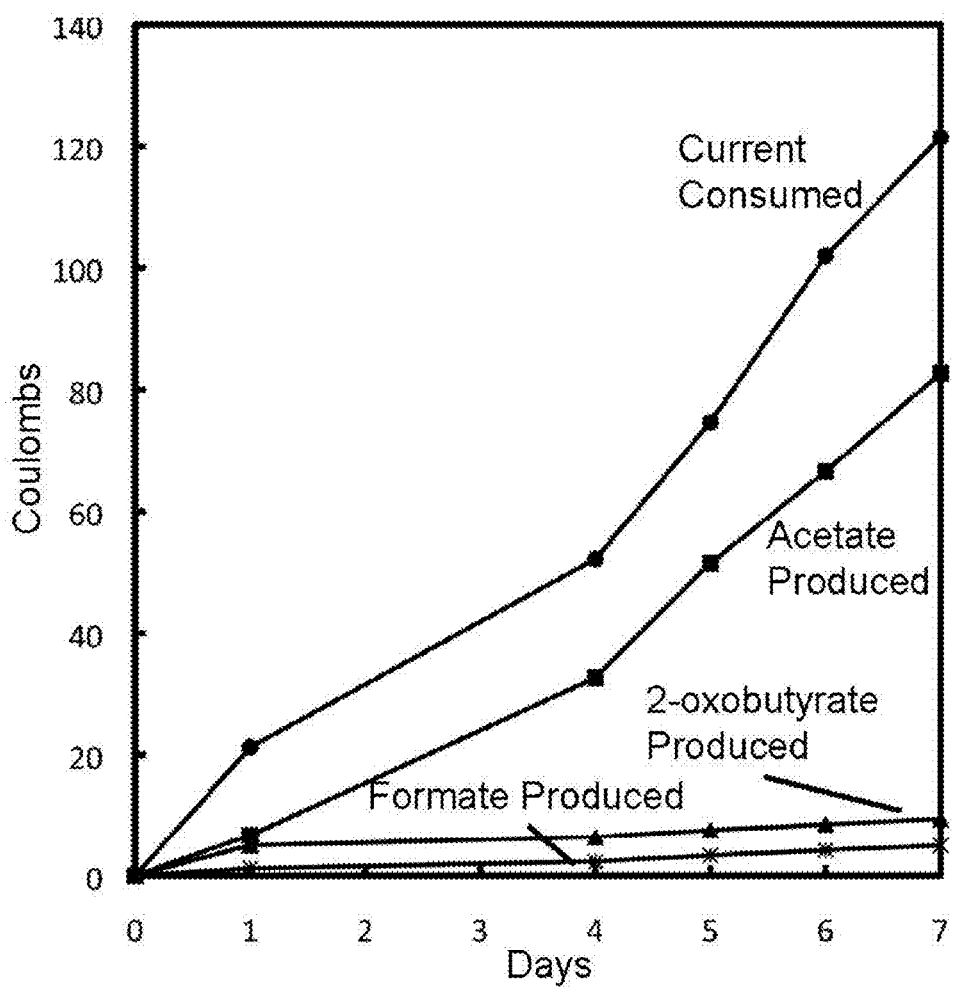
FIG. 13 shows electron consumption and product formation of a biofilm of *Clostridium ljungdahlii* over time. Results shown are from a representative example of three replicate cultures.
Figures 14A, 14B:
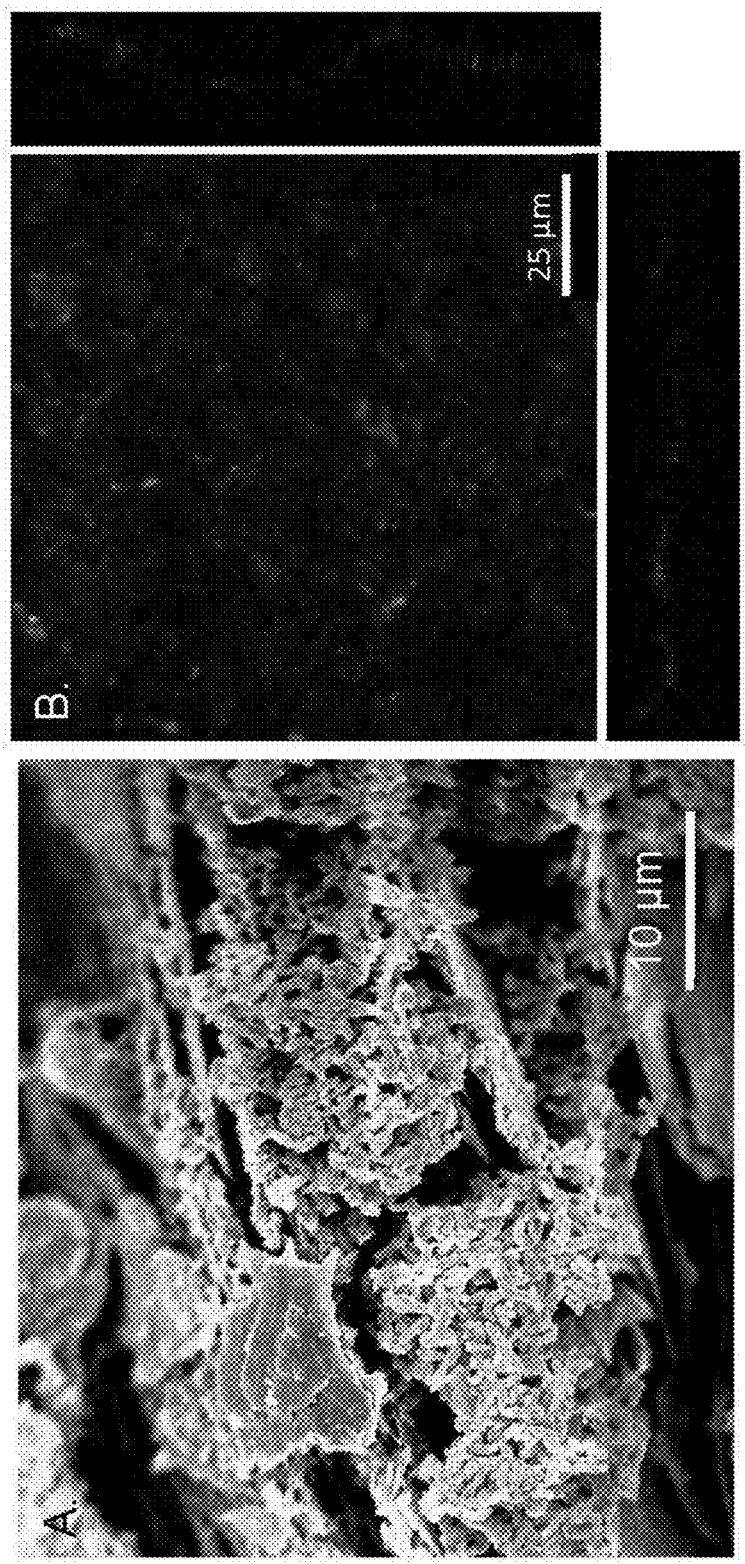
FIG. 14A shows a scanning electron micrograph of a cathode biofilm of *Clostridium ljungdahlii*.
FIG. 14B shows confocal scanning laser microscopy top down and side view images of cathode biofilm of *Clostridium ljungdahlii* biofilm after 14 days. Cells were stained with LIVE/DEAD BacLight viability stain.

*Clostridium ljungdahlii* consumed current with a concomitant accumulation of acetate and minor production of formate and 2-oxobutyrate over time (FIG. 13). Electron recovery in these products accounted for 82±10% of the electrons consumed with 88±2% of these electrons appearing in acetate. Scanning electron microscopy (FIG. 14A) and confocal scanning laser microscopy (FIG. 14B) revealed a thin layer of metabolically active cells were on the cathode surface, similar to the cathode biofilms of the *Sporomusa* strains.

Figure 15:
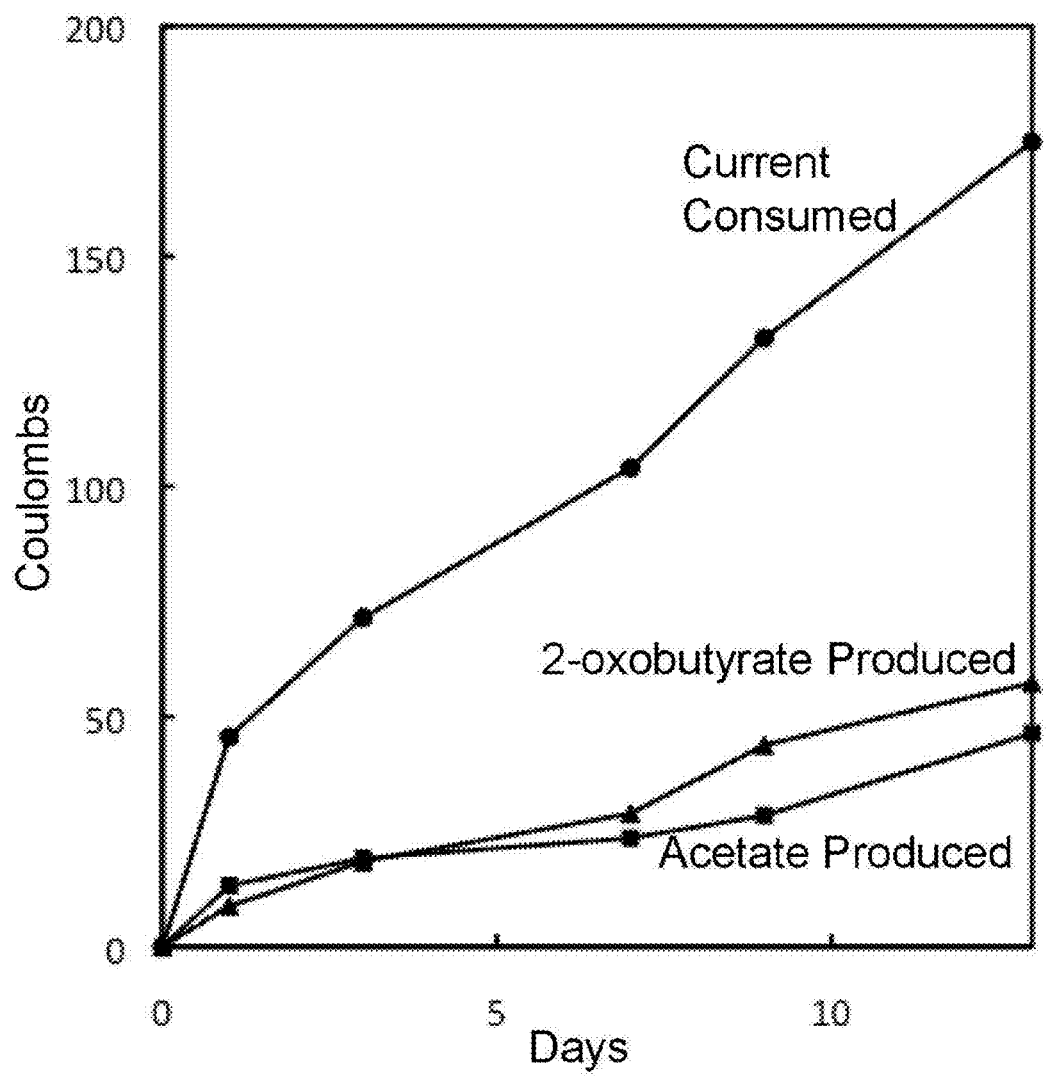
FIG. 15 shows electron consumption and product formation of a biofilm of *Clostridium aceticum* over time. Results shown are from a representative example of two replicate cultures.

*Clostridium aceticum* consumed current more slowly than *C. ljungdahlii* (FIG. 15). Unlike any of the other cultures evaluated 2-oxobutyrate was as important a product as acetate. Recovery of electrons consumed in acetate and 2-oxobutryate was low (53+4%) This poor recovery is attributed to the formation of other products that have yet to be identified. As with the other strains evaluated only a thin biofilm developed, with little protein (0.030±0.002 mg/cm²) recovered from the cathode surface.

Figure 16:
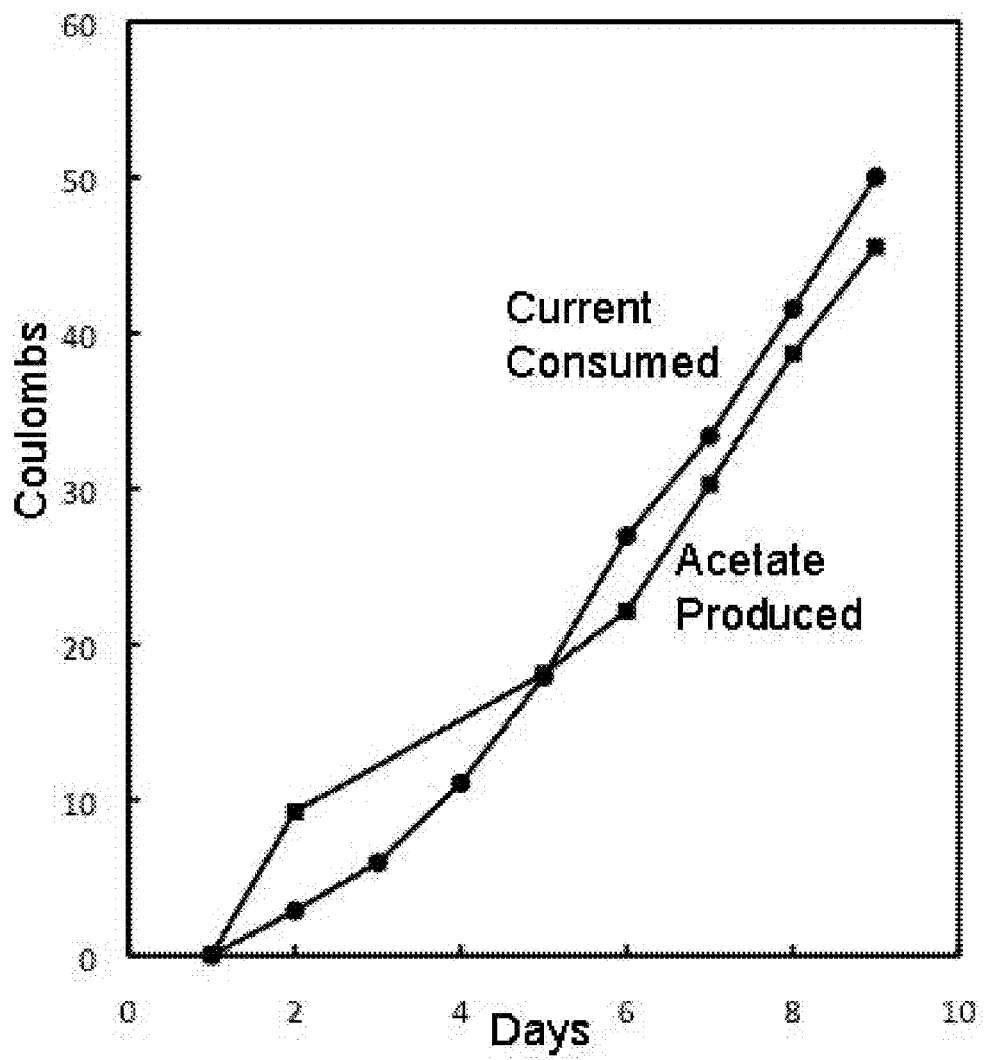
FIG. 16 shows electron consumption and product formation of a biofilm of *Moorella thermoacetica* over time. Results shown are from a representative example of three replicate cultures.

*Moorella thermoacetica* was able to draw current with the production of mainly acetate (FIG. 16). The electron recovery was 85+7%.

*Acetobacterium woodii* was the only acetogen tested that appeared unable to accept electrons from an electrode. More than ten attempts to establish cultures on the cathode failed.

Enrichment Cultures

Figure 18:
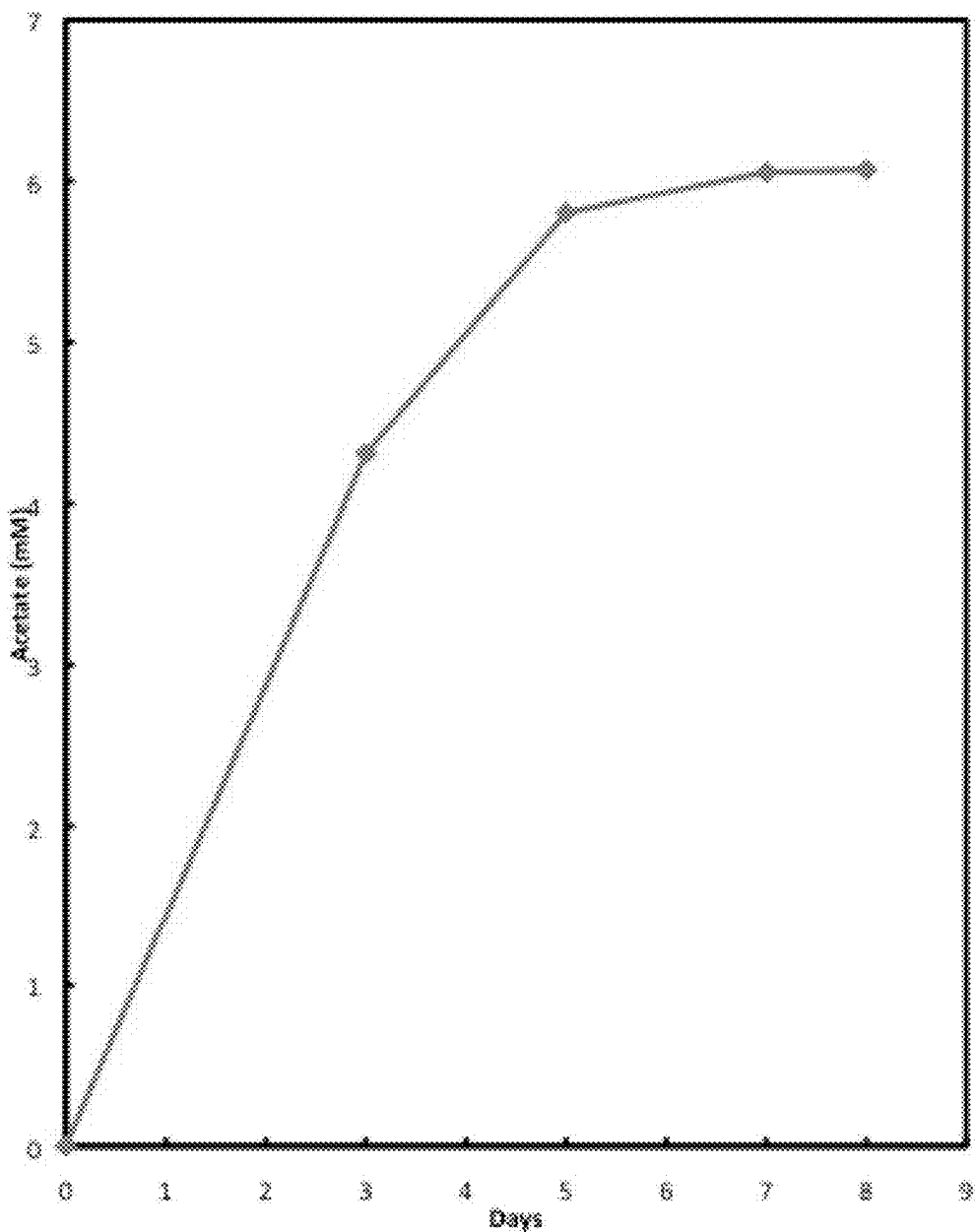
FIG. 18 shows the production of acetate from carbon dioxide with a mixture of microorganisms obtained from plant rhizosphere.

None of the environmental samples were as effective as the pure cultures capable of electrosynthesis. For example, as illustrated in FIG. 18 rhizosphere inocula initially produced acetate, but acetate production was not sustained when the medium was partially (50%) replaced to begin the enrichment process.

Mechanisms for Electron Transfer and Energy Conservation

It appeared that all of the strains that consumed current were directly accepting electrons from the electrode surface, without hydrogen serving as an electron carrier between the cathode and the cells. There was no accumulation of hydrogen with poised cathodes in the absence of microorganisms. Low, steady-state concentrations (10-100 ppm) of hydrogen were detected when cells were consuming current. This is attributed to the fact that metabolically active anaerobic microorganisms with hydrogenases produce hydrogen to levels that reflect the redox status of the cells. These hydrogen levels were well below the >400 ppm that acetogenic microorganisms require for acetogenesis. Further evidence for a lack of hydrogen production was the finding that *A. woodii*, which was able to reduce electron carbon dioxide with hydrogen as the electron donor in the cathode chamber, did not metabolize once the hydrogen was removed. Previous studies with *Geobacter* species at only slightly higher potentials also suggested that hydrogen was not an intermediate in electron transfer from electrodes to cells, due to the ability of strains unable to use hydrogen to function just was well as hydrogen-utilizing strains and the lack of up-regulation of hydrogenase genes during growth on the cathode.

The mechanisms by which electrons may be directly transferred from electrodes to these microorganisms and then onto reduction of carbon dioxide is not known. The mechanisms for electron transfer from microorganisms to electrodes have been studied in detail in two microorganisms, *S. oneidensis* and *G. sulfurreducens*, which appear to have significantly different strategies for electronically interacting with electrodes. There is strong evidence that *S. oneidensis* produces electron shuttles that promote electron transfer from cells to the electrode. Although it has been proposed that *S. oneidensis* might establish direct electrical contact with electrodes via cytochromes associated with conductive filaments, this speculation is not consistent with electrochemical analysis of *S. oneidensis* biofilms, the production of significant current by planktonic cells in *S. oneidensis* fuel cells, or the finding that deleting genes for pilin formation have no impact on the capacity for current production. In contrast, when producing current, *G. sulfurreducens* establishes a direct electrical contact with electrodes and gene expression and gene deletion studies, as well as measurements of biofilm conductivity and protein localization suggest that electrons are transported through the anode biofilm along conductive pili with c-type cytochromes aiding in electron transfer from the biofilm to the anode. Surprisingly, gene expression patterns in *G. sulfurreducens* consuming current are significantly different than those in current-producing biofilms and deletion of genes that are essential for optimal current production have no impact on current consumption and vice versa. These results suggest that electron transfer from electrodes into cells may be different than those for current production. Although it is often considered that gram positive microorganisms capable of current production donate electrons to electrodes via electron shuttles, direct electronic interaction is possible. Further investigation will be required before it will be possible to speculate on how acetogens described here can accept electrons from cathodes.

The inability of *A. woodii* to function on the cathode is consistent with a working model for how acetogenic microorganisms may conserve energy with electrons directly derived from cathodes serving as the electron donor. In this model, the reduction carbon dioxide to organic acids in the cytoplasm consumes protons, generating a proton gradient, and ATP is generated with proton-dependent ATPases. *A. woodii* would not be able to conserve energy in this manner because it contains sodium-dependent ATPases.

These results demonstrate that a wide diversity of microorganisms are capable of reducing carbon dioxide to organic acids with electrons derived from an electrode. Although microbial electrosynthesis has potential to be an environmentally sustainable approach for the large-scale production of fuels and other chemicals from carbon dioxide, for this to be a practical process microorganisms that are capable of electrosynthesis preferably are genetically tractable to permit engineering metabolism for the generation of desired products and preferably are hardy enough for an industrial process. For example, *C. ljungdahlii* has already been engineered to produce small amounts of butanol. Electrodes are not natural extracellular interfaces for microorganisms. Adaptive evolution has proven to be an effective strategy for improving the rates of electron exchange between microorganisms and external electron acceptors.

Definitions

Definition of Oxidation

Oxidation is defined as the interaction between oxygen molecules and all the different substances they may contact, from metal to living tissue. Technically, however, with the discovery of electrons, oxidation came to be more precisely defined as the loss of at least one electron when two or more substances interact. Those substances may or may not include oxygen. (Incidentally, the opposite of oxidation is reduction—the addition of at least one electron when substances come into reactive contact with each other.)

Examples:

Oxidation of Metal M to metal ion:

$$M \rightarrow M^+ + e^-$$

Reduction of metal ion to metal M:

$$M^+ + e^- \rightarrow M$$

Oxidation of oxide ion:

$$O^{2-} \rightarrow O + 2e^-$$

Reduction of Oxygen:

$$O + 2e^- \rightarrow O^{2-}$$

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. An apparatus for generating a carbonaceous chemical wherein carbon dioxide is a source of carbon, comprising:
a reaction vessel having an anode electrode and a cathode electrode disposed therein, said anode electrode having at least one surface and an anode electrical contact terminal, said cathode electrode having at least one surface and a cathode electrical contact terminal, said cathode electrode having a film of biologically active material comprising at least one bacterium adjacent said at least one surface of said cathode electrode and in electrical communication therewith, said biologically active material and said cathode configured to generate a carbonaceous chemical that comprises at least two carbon atoms, said anode configured to generate molecular oxygen, said reaction vessel configured to contain a working fluid having mobile ions therein;
a reaction medium in contact with said cathode electrode and said anode electrode, said reaction medium configured to contain a substance configured to be oxidized;
a source of electrical energy, said source of electrical energy electrically connected to said cathode electrical contact terminal and to said anode electrical contact terminal; and
a source of carbon dioxide configured to provide carbon dioxide to said film of biologically active material adjacent said at least one surface of said cathode electrode by way of said reaction medium.

2. The apparatus for generating a carbonaceous chemical wherein carbon dioxide is a source of carbon of claim 1, wherein said reaction vessel has a first chamber and a second chamber, said first chamber and said second chamber each configured to contain a working fluid having mobile ions therein, said first chamber and said second chamber separated by a membrane permeable to at least a selected ionic species, said anode electrode disposed in one of said first chamber and said second chamber and said cathode electrode disposed in the other of said first chamber and said second chamber.

3. The apparatus for generating a carbonaceous chemical wherein carbon dioxide is a source of carbon of claim 1, wherein said film of biologically active material comprises an organism that is able to generate a carbonaceous chemical having at least two carbon atoms using carbon dioxide as a source of carbon.

4. The apparatus for generating a carbonaceous chemical wherein carbon dioxide is a source of carbon of claim 1, wherein said carbonaceous chemical comprises carbon, hydrogen and oxygen.

5. The apparatus for generating a carbonaceous chemical wherein carbon dioxide is a source of carbon of claim 1, wherein said working fluid having mobile ions therein is a source of a chemical species configured to be oxidized.

6. The apparatus for generating a carbonaceous chemical wherein carbon dioxide is a source of carbon of claim 1, further comprising:
a control module configured to control a selected one of an electrical potential applied between said cathode electrode and said anode electrode, and an electrical current caused to flow between said cathode electrode and said anode electrode.

7. The apparatus for generating a carbonaceous chemical wherein carbon dioxide is a source of carbon of claim 6, further comprising:
a third electrode having a third electrical contact terminal in electrical communication with said control module, said third electrode configured to provide a reference potential relative to a selected one of said cathode electrode and said anode electrode.

8. The apparatus for generating a carbonaceous chemical wherein carbon dioxide is a source of carbon of claim 1, wherein at least one of said cathode electrical contact terminal and said anode electrical contact terminal is external to said vessel.

9. The apparatus for generating a carbonaceous chemical wherein carbon dioxide is a source of carbon of claim 1, wherein said source of electrical energy is a renewable energy source.

10. The apparatus for generating a carbonaceous chemical wherein carbon dioxide is a source of carbon of claim 9, wherein said renewable energy source is selected from the group consisting of a solar cell, solar thermal energy, wind energy, geothermal energy, hydroelectricity, and a biomass-fired electrical generator.

11. The apparatus for generating a carbonaceous chemical wherein carbon dioxide is a source of carbon of claim 10, wherein said solar cell is selected from the group consisting of photovoltaic solar cells and photoelectrochemical solar cells.

12. The apparatus for generating a carbonaceous chemical wherein carbon dioxide is a source of carbon of claim 1, wherein said source of carbon dioxide is selected from the group consisting of carbon dioxide in an effluent from a combustion process of coal, petroleum, methane, natural gas, biomass, organic carbon, an industrial process that releases carbon dioxide, carbon dioxide from geothermal sources, atmospheric $CO_2$, $CO_2$ from dry ice, $CO_2$ from carbonate minerals, $CO_2$ from carbonic acid ($H_2CO_3$), and $CO_2$ sequestered from the atmosphere.

13. The apparatus for generating a carbonaceous chemical wherein carbon dioxide is a source of carbon of claim 1, further comprising a source of ionic hydrogen and a source of ionic oxygen.

14. The apparatus for generating a carbonaceous chemical wherein carbon dioxide is a source of carbon of claim 13, wherein said source of ionic hydrogen and said source of ionic oxygen is water.

15. The apparatus for generating a carbonaceous chemical wherein carbon dioxide is a source of carbon of claim 1, wherein at least one of said cathode electrode and said anode electrode comprises a material selected from the group consisting of carbon paper, carbon cloth, carbon felt, carbon wool, carbon foam, graphite, porous graphite, graphite powder, graphene, carbon nanotubes, electrospun carbon fibers, a conductive polymer, platinum, palladium, titanium, gold, silver, nickel, copper, tin, iron, cobalt, tungsten, stainless steel, and combinations thereof.

16. The apparatus for generating a carbonaceous chemical wherein carbon dioxide is a source of carbon of claim 1, wherein said apparatus is configured to perform a net chemical reaction that is described by the equation $$M\ CO_2 + N\ H_2O \rightarrow C_M H_Y O_Z + P\ O_2$$

where M, N and P are non-negative numbers and Y=2N, and Z=2M+N−2P.

17. The apparatus for generating a carbonaceous chemical wherein carbon dioxide is a source of carbon of claim 1, wherein said apparatus is configured to perform a net chemical reaction that is described by the equation $2\ CO_2 + 2\ H_2O \rightarrow CH_3COOH + 2\ O_2$.

18. The apparatus for generating a carbonaceous chemical wherein carbon dioxide is a source of carbon of claim 1, wherein said apparatus is configured to perform a net chemical reaction that is described by the equation $4CO_2 + 5\ H_2O \rightarrow \text{Butanol}\ (C_4H_{10}O) + 6\ O_2$.

* * * * *